United States Patent [19]

Byker

[11] Patent Number: 5,751,467
[45] Date of Patent: *May 12, 1998

[54] VARIABLE REFLECTANCE AUTOMOBILE MIRROR

[75] Inventor: Harlan J. Byker, Holland, Mich.

[73] Assignee: Gentex Corporation, Zeeland, Mich.

[*] Notice: The portion of the term of this patent subsequent to Jul. 7, 2009, has been disclaimed.

[21] Appl. No.: 874,175

[22] Filed: Apr. 23, 1992

Related U.S. Application Data

[60] Continuation of Ser. No. 760,877, Sep. 16, 1991, abandoned, which is a division of Ser. No. 422,601, Oct. 17, 1989, abandoned, which is a division of Ser. No. 846,354, Mar. 31, 1986, Pat. No. 4,902,108.

[51] Int. Cl.$^6$ .................................................. G02F 1/153
[52] U.S. Cl. ........................ 359/272; 359/265; 359/267; 359/269; 359/270; 359/274; 359/321
[58] Field of Search .......................... 359/265, 267, 359/269, 270, 272, 274, 321

[56] References Cited

U.S. PATENT DOCUMENTS

| | | | |
|---|---|---|---|
| 3,280,701 | 10/1966 | Donnelly et al. | 88/77 |
| 3,451,741 | 6/1969 | Manos | 350/160 |
| 3,692,388 | 9/1972 | Hall et al. | 350/312 |
| 3,806,229 | 4/1974 | Schoot et al. | 350/160 LC |
| 3,807,832 | 4/1974 | Castellion | 350/160 R |
| 3,873,185 | 3/1975 | Rogers | 350/147 |
| 4,090,782 | 5/1978 | Bredfeldt et al. | 350/357 |
| 4,093,358 | 6/1978 | Shattuck et al. | 350/357 |
| 4,139,276 | 2/1979 | Clecak et al. | 350/357 |
| 4,435,048 | 3/1984 | Kamimori et al. | 359/275 |
| 4,752,119 | 6/1988 | Ueno et al. | 350/357 |
| 5,128,799 | 7/1992 | Byker | 359/265 |

FOREIGN PATENT DOCUMENTS

| | | |
|---|---|---|
| 0 012419 | 6/1980 | European Pat. Off. |
| 57-30639 | 2/1982 | Japan . |
| 57-208530 | 12/1982 | Japan . |
| 566863 | 8/1977 | U.S.S.R. |

OTHER PUBLICATIONS

Reexamination Control No. 90/003254.
Ushakov et al. (I) , "A Calculation of Steady-State Electrocoloration Parameters of Electrochromic Systems", Elektrokhimiya, 21, 918–922 (1985) (translation).
Ushakov et al. (II), "Electrochromism of Organic Compounds Some Properties of Two–Electrode Cells", Elecktrokmihiya, 14, 319–322 (1978) (translation).
Shelepin et al. (I), "Electrochromism of Organic Compounds I. Electrochemical and Spectral Properties of A System Based on Methylviologen and 3–Ethyl–2–Benzothiazolone Azine", Elektrokhimiya, 13, 32–37 (1977) (translation).
Shelepin et al. (II), "Electrochromism of Organic Compounds II. Spectral and Electrochemical Examination Of A System Based on Methylviologen and 5,10–Dihydro–5,10–Dimethylphenazine", Elektrokhimiya, 13, 404–408 (1977) (translation).
Chang, "Electrochromic and Electrochemichromic Materials and Phenomena" in Kmetz and von Willison, eds., *Non–emissive Electrooptic Displays*, Pergamon Press, New York, 1976, pp. 155–196.

(List continued on next page.)

*Primary Examiner*—Georgia Y. Epps
*Assistant Examiner*—Evelyn A. Lester
*Attorney, Agent, or Firm*—Brian J. Rees

[57] ABSTRACT

The present invention provides variable reflectance automobile mirrors wherein the component of variable transmittance is a single-compartment, self-erasing, solution-phase electrochromic device.

109 Claims, 2 Drawing Sheets

OTHER PUBLICATIONS

Ueno et al., "Three Color Switching Electrochromic Display Using Organic Redox-Pair Dyes", Japan J. Appl. Phys. 24, L178–L180 (Mar., 1985).

Shelepin & Ushakov, "Photochemical and Cathodic Reduction of Methyl Viologen in Solution," Russian J. Phys. Chem. 49, 1021–1024 (1975) (translation).

Gruver and Kuwana, "Spectroelectrochemical Studies of E.E. and E.E.C. Mechanisms," J. Electroanal. Chem. 36, 85–94 (1972).

Strojek et al., "Direct Log Ratio Recording, Rapid Scanning Spectrophotometer," Anal. Chem., 41, 481–484 (1969).

Nelson et al., "Anodic Oxidation of 5,10–Dihydro–5, 10–Dimethylphenazine," Z. Anal. Chem. 224, 184–196 (1967).

VARIABLE REFLECTANCE AUTOMOBILE MIRROR

This application is a continuation of application Ser. No. 07/760,877, filed Sep. 16, 1991, abandoned, which is a division of Ser. No. 07/422,601, filed Oct. 17, 1989, abandoned, which is a division of application Ser. No. 06/846,354, filed Mar. 31, 1986, now U.S. Pat. No. 4,902,108.

TECHNICAL FIELD

The present invention relates to devices of reversibly variable transmittance to electromagnetic radiation, compositions for use as media of reversibly variable transmittance in such devices, and use of such devices in variable transmission light filters and variable reflectance mirrors. More particularly, the invention relates to single-compartment, self-erasing, solution-phase electrochromic devices, solutions for use therein and uses thereof.

BACKGROUND OF THE INVENTION

Several different types of devices are known wherein transmittance to electromagnetic radiation can be reversibly varied. Among such devices are those wherein the transmittance is changed by thermochromic, photochromic, or electro-optic (e.g., liquid crystal, dipolar suspension, electrophoretic, electrochromic) means and wherein the variable transmittance is to electromagnetic radiation that is at least partly in the visible range (wavelength from 4200Å to 7000Å).

Devices of reversibly variable transmittance to electromagnetic radiation have found application as the variable transmittance element in variable transmittance light-filters, variable reflectance mirrors, and display devices which employ such light-filters or mirrors in conveying information. These variable transmittance light filters have included windows. The variable reflectance mirrors have included anti-glare rearview mirrors for automotive vehicles.

Devices of reversibly variable transmittance to electromagnetic radiation, wherein the transmittance is altered by electrochromic means, including electrochemichromic devices, are described, for example, by Chang, "Electrochromic and Electrochemichromic Materials and Phenomena," in Non-emissive Electro-optic Displays, A. Kmetz and K. von Willisen, eds. Pergamon Press, New York, New York 1976, pp. 155–196 (1976). Electrochemichromic devices includes those wherein electrochemical reactions occur in a solid film, involve electroplating or occur entirely in solution. See Chang, supra.

Numerous electrochemichromic devices are known in the art. See, e.g., Manos, U.S. Pat. No. 3,451,741; Bredfeldt et al., U.S. Pat. No. 4,090,782; Shattuck and Sincerbox, U.S. Pat. No. 4,093,358; Clecak et al., U.S. Pat. No. 4,139,276; Kissa et al., U.S. Pat. No. 3,453,038; Rogers, U.S. Pat. Nos. 3,652,149, 3,774,988 and 3,873,185; and Jones et al., U.S. Pat. Nos. 3,282,157, 3,282,158, 3,282,160 and 3,283,656. Among these devices are single-compartment, self-erasing, solution-phase electrochromic devices. See, e.g., Manos, supra, which is incorporated herein by reference; Bredfeldt et al., supra; Shattuck and Sincerbox, supra; and Clecak et al., supra.

In a single-compartment, self-erasing, solution-phase electrochromic device, the intensity of electromagnetic radiation is modulated by passing through a solution held in the device in a compartment which includes two electrodes. The two electrodes are in contact with the solution. Between the electrodes, there is no barrier, such as a semi-permeable membrane, which would divide the solution compartment and prevent some components in the solution from diffusing or migrating from one electrode to the other. The solution includes a solvent and at least one "anodic" compound (which can be neutral or charged) and at least one "cathodic" compound (which also can be neutral or charged). The "anodic" compounds are electrochemically oxidized and the "cathodic" compounds are electrochemically reduced when a DC electrical potential difference is impressed across the solution between the electrodes. If none of the "anodic" compounds and "cathodic" compounds to be oxidized or reduced is charged, prior to oxidation or reduction, respectively, the solution will, and otherwise the solution may, include inert, current-carrying electrolyte. The electrochemical properties of the solvent, inert, current-carrying electrolyte, if any, anodic compounds, cathodic compounds, and any other components that might be present in the solution are preferably such that the anodic and cathodic compounds are oxidized and reduced, respectively, at a potential difference between the electrodes which does not cause any significant electrochemical or other changes in the other components in the solution. The solution is fluid during operation of the device, although it may be gelled or made highly viscous with a thickening agent. That the devices are "solution-phase" means that all of the components in the solution, including the anodic and cathodic compounds, remain in solution during operation of the device with the concomitant oxidation of anodic compounds and reduction of cathodic compounds.

Reversible modulation of intensity of electromagnetic radiation passing through a single-compartment, self-erasing, solution-phase electrochromic device can be accomplished because of three factors related to operation of the device. First, the molar extinction coefficients of the anodic compounds and cathodic compounds in the solution of the device, as a function of wavelength, change with their electrochemical oxidation and reduction, respectively. Generally, at least one of these compounds undergoes a significant change in extinction coefficient at wavelengths in the visible range upon the oxidation or reduction; consequently, the solution and device change color or change from dark to clear or clear to dark when a potential difference is applied across the solution between the electrodes. Second, in the solution, the oxidized anodic compounds and reduced cathodic compounds do not, to any significant extent, undergo degradative reactions unimolecularly or with other components. Third, in the solution, the oxidized anodic compounds react substantially only with the reduced cathodic compounds to yield substantially only anodic compounds and cathodic compounds in their forms and with their properties prior to the oxidations and reductions, respectively. These reactions of oxidized anodic compounds with reduced cathodic compounds provide the "self-erasing" feature to the device.

Heretofore, no single-compartment, self-erasing, solution-phase electrochromic devices have been known which have proven to be suitable for commercial application as the component of reversibly variable transmittance in variable transmittance light filters or variable reflectance mirrors. For such applications, the solution of variable transmittance must be highly stable to cycling, at least several thousands of times, from zero potential difference between the electrodes to a potential difference between the electrodes that is sufficient to cause significant change in transmittance and then back to zero again. In a typical device, the solution is held in a layer between planar, parallel, spaced-apart, transparent walls, on the inside surfaces of which (in contact with the solution) are coated thin layers of transparent, electrically conductive material which serve as electrodes and through which passes electromagnetic radiation whose intensity is reversibly modulated in the device. It is advantageous to have the solution layer as thin as possible, in order to minimize distortion of light passing through, or passing into and reflecting out of, a device, and to reduce to durations that are acceptable for commercial applications the "response time" required for the transmittance of a device to achieve a new steady-state value when the potential difference between the electrodes is changed. However, for devices with thin solution layers, anodic and cathodic electrochromic compounds must be found that, at concentrations in the solution at which they remain soluble, both at zero-potential equilibrium and when oxidized (in the case of anodic compounds) and reduced (in the case of cathodic compounds) when a potential difference is applied between the electrodes, give rise to sufficiently large changes in absorbance between their zero-potential equilibrium states and their "activated" (i.e., oxidized or reduced) states and at the same time remain sufficiently stable to cycling to provide a commercially practicable device. The present invention addresses the need for solutions to make commercially practicable single-compartment, self-erasing, solution-phase electrochromic devices.

A useful feature in such devices, that has not heretofore been available, is the capability to function as a gray-scale device, i.e., to vary continuously and rapidly in transmittance to light in the visible wavelength range as a function of the potential difference applied between the electrodes of the device. Such a "gray-scale" device would find application in a window, which would allow light of constant intensity to pass through independently of the intensity of the light reaching the window, and an anti-glare rearview mirror in an automobile, that would reflect light of acceptable intensity to the driver regardless of the intensity of the glare-causing light incident on the mirror from headlamps of automobiles approaching the vehicle from behind. The present invention provides gray-scaling capability in single-compartment, self-erasing, solution-phase electrochromic devices.

A problem that has not heretofore been recognized with solution-phase electrochromic devices is segregation, due to both migration and natural convection of anodic and cathodic electrochromic compounds. Particularly in devices that are operated continuously for long periods (more than about 20 minutes) with the planar surface through which light enters the device oriented vertically to the ground, such segregation can cause annoying and troublesome separation of color and reduction in speed of self-erasing. The present invention addresses this segregation problem.

Variable reflectance mirrors include a variable transmittance component, which is a device which has a transmittance to visible light which is reversibly varied by thermochromic, photochromic, or electro-optic means, and a reflection means, which is a highly reflective surface (such as a silver layer) from which light is reflected after passing through a medium of reversibly variable transmittance in the variable transmittance component. After reflecting from the reflection means, the reflected light passes back through the medium of reversibly variable transmittance. The medium of variable transmittance in such mirrors is typically held, in the variable transmittance component, between two planar, parallel, spaced-apart surfaces. At least one of these surfaces is transparent to light, and light reflected by the mirror enters and leaves through this transparent surface. A problem with such mirrors is the high "residual" reflectivity, which is usually greater than 5%, of this transparent surface of the variable transmittance component. For example, in an anti-glare rearview mirror for an automobile, wherein elimination of high glare may require reduction of reflectivity observed by the driver from all surfaces to as low as about 5 to 7%, the high residual reflectivity of the front surface of a typical mirror requires that the transmittance of the medium of reversibly variable transmittance in the mirror be capable of being made as low as about 3%. Because it is difficult to achieve such low transmittance with sufficient speed in preferably thin devices of reversibly variable transmittance, it would be advantageous to have variable reflectance mirrors wherein these problems caused by high residual reflectivity are avoided. The present invention provides such mirrors.

SUMMARY OF THE INVENTION

The present invention provides solutions for use as the medium of reversibly variable transmittance to electromagnetic radiation, particularly light in the visible range, in single-compartment, self-erasing, solution-phase electrochromic devices.

The invention provides further such electrochromic devices, wherein a solution of the invention is the medium of reversibly variable transmittance; variable transmission light filters and variable reflectance mirrors, wherein the variable transmittance component is a single-compartment, self-erasing, solution-phase device according to the invention; and display devices wherein information is displayed by operation of variable transmission light filters or variable reflectance mirrors according to the invention.

The solutions of the invention render commercially practical the use of single-compartment, self-erasing, solution-phase electrochromic devices and variable transmission light filters, variable reflectance mirrors and display devices employing such filters and mirrors. The solutions of the invention are unexpectedly highly stable to cycling of potential differences between the electrodes in devices of the invention.

In devices of the invention wherein the solution layer is desirably thin, and with concentrations of anodic and cathodic compounds in the solution that are low enough that precipitation does not occur and problems of segregation are substantially reduced, and at potential differences between the electrodes that are low enough to avoid significant degradation of the solution, the solutions of the invention darken to an unexpectedly high absorbance to visible light with unexpectedly high speed once the potential difference is applied and clear again with unexpectedly high speed once the electrodes are open-circuited or short-circuited. Advantageously, reversal of the polarity of the electrodes of a device of the invention is not required for clearing to occur with sufficient speed for many practical applications. Further, devices of the invention can advantageously be operated as gray-scale devices.

In another aspect, the present invention entails novel electrochromic compounds and combinations of compounds for use in solutions of the invention.

In still another aspect, the invention includes an improved variable reflectance mirror, wherein variable reflectance is provided by thermochromic, photochromic, or electro-optic means in a device of variable transmittance to electromagnetic radiation. In such an improved mirror of the invention, problems due to residual reflectivity from a planar surface through which light enters, and after reflecting from the reflecting means, leaves the mirror are avoided by displacing this planar surface at a slight angle to the highly reflective planar surface of the mirror which is its reflecting means. Thereby, a person viewing the mirror need not see light due to residual reflectivity simultaneously with light that is reflected from the mirror's reflecting means.

BRIEF DESCRIPTION OF THE DRAWINGS

FIG. 2 shows, by cross-hatched area 14, the portion, of planar, transparent side 100 of the device, which overlays the solution of reversibly variable transmittance in the device and which, consequently, changes color, or changes from clear to dark and back, as the device is operated.

DETAILED DESCRIPTION OF THE INVENTION

Figure 1:
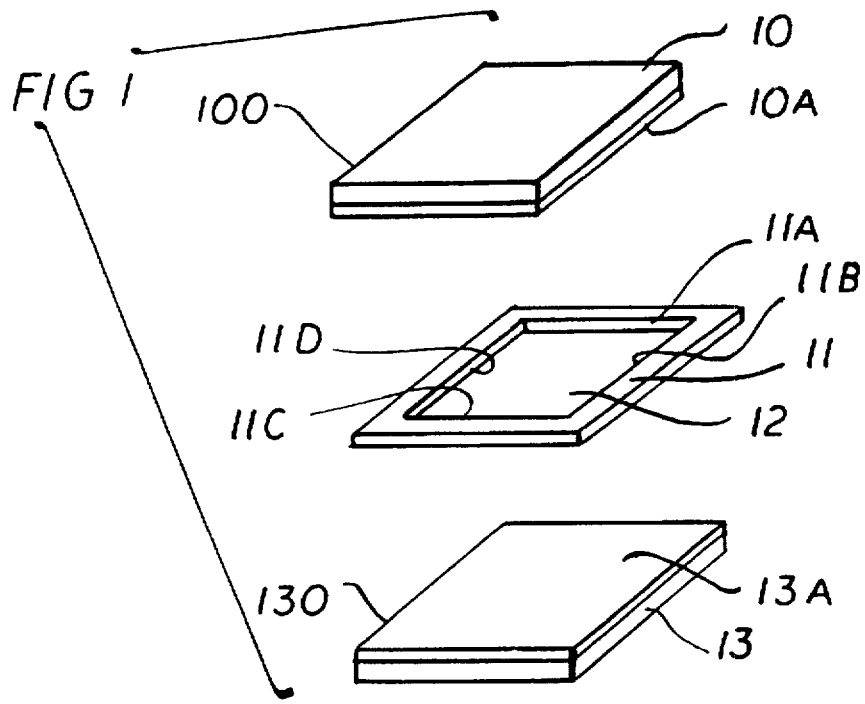
FIG. 1 displays schematically an exploded view of two planar, transparent, electrode-bearing sides, 100 and 130, of a device of the invention together with spacer or separating means, 11, which holds the electrode-bearing sides apart and substantially parallel in an assembled device of the invention and the inside edges, 11A, 11B, 11C and 11D of which, together with the electrode layers, 10A and 13A, of the electrode-bearing sides, defines a space, 12, which, in an assembled device of the invention, is occupied by a solution according to the invention that is in contact with the electrode layers.

In one of its aspects, the present invention is a solution, for use as the variable transmittance medium in a single-compartment, self-erasing, solution-phase electrochromic device, which comprises:

(A) a solvent;

(B) at least one cathodic electrochromic compound which, in a voltammogram done with an inert electrode in the solvent at room temperature, displays at least two chemically reversible reduction waves, with the first of said reductions accompanied by an increase in molar extinction coefficient at at least one wavelength in the visible range;

(C) at least one anodic electrochromic compound which, in a voltammogram done with an inert electrode in the solvent at room temperature, displays at least two chemically reversible oxidation waves, with the first of said oxidations accompanied by an increase in molar extinction coefficient at at least one wavelength in the visible range; and (D) if all cathodic and anodic compounds in their zero-potential equilibrium states in the solution are not ionic, an inert current-carrying electrolyte.

The solutions of the invention are optionally gelled or thickened by being combined with an agent, such as acrylic sheet material thickner, derived from, for example, the acrylic sheet material sold under the trademark LUCITE L®.

In another of its aspects, the instant invention is a single-compartment, self-erasing, solution-phase electrochromic device which comprises, as the medium of reversibly variable transmittance to light, a solution of the invention. The solution of reversibly variable transmittance in a device of the invention is optionally gelled or thickened.

In another aspect, the present invention entails a variable transmittance light-filter which comprises, as the variable transmittance element, a single-compartment, self-erasing, solution-phase device of the invention.

In a further aspect, the invention entails a variable reflectance mirror which comprises, as the variable transmittance element, a single-compartment, self-erasing, solution-phase device of the invention.

In a still further aspect, the invention includes a display device which comprises, as an information-conveying element, a variable transmittance light filter or variable reflectance mirror according to the invention.

In another aspect, the invention includes a compound of Formula LII

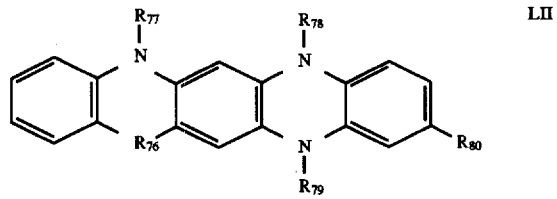

wherein $R_{76}$ is oxygen or sulfur, $R_{80}$ is hydrogen or dialkylamino, wherein the alkyl groups are the same or different and are each of 1 to 6 carbon atoms, and $R_{771}$, $R_{78}$ and $R_{79}$ are the same or different and are each selected from hydrogen, alkyl of 1 to 6 carbon atoms, phenyl optionally substituted at any one position with an alkyl group of 1 to 6 carbon atoms, and benzyl, optionally substituted at any one position of the phenyl group with an alkyl group of 1 to 6 carbon atoms.

In still another aspect, the present invention includes a variable reflectance mirror which comprises a device of reversibly variable transmittance, a planar front surface, and a planar reflecting means, (A) said device comprising (i) a medium of transmittance which is reversibly varied by thermochromic, photochromic, or electro-optic means, and (ii) two planar, parallel, spaced-apart surfaces, between which the medium of reversibly variable transmittance is held and through which light passes prior to and after reflecting from said reflecting means; with (B) the angle between the plane of said front surface and the plane of said reflecting means being about 1° to about 5°.

In the mirrors, a significant improvement arises from the positioning of the plane of the reflecting means at a slight angle to the plane of the front surface of the mirror, i.e., the surface through which light reflected by the mirror from the reflecting means enters and leaves the mirror. This positioning of these planes permits the mirror to be oriented so that light from outside the mirror that is reflected from the front surface of the mirror without entering the mirror (i.e., light from residual reflectivity of the front surface) is not seen by the person using the mirror while light reflected from the reflecting means is seen by such person. Thus, to reduce reflection (including reflected glare) from such a mirror, the residual reflectivity of the front surface of the mirror does not need to be overcome and, consequently, the extent to which the medium of reversibly variable transmittance needs to be darkened is reduced in comparison with the darkening that would be required if the reflecting means were parallel to the front surface. Further, various distortions in reflected images that occur, when both light reflected due to residual reflectivity of the front surface of a mirror and light reflected from the reflecting means of the mirror are observed, are avoided when only light from the reflecting means is seen.

Although any medium whose transmittance to visible light can be reversibly altered by thermochromic, photochromic, or electro-optic means can be employed as the medium of reversibly variable transmittance in these improved mirrors of the invention, it is most preferred that the medium be a solution according to the present invention (optionally gelled or thickened) and that the device of reversibly variable transmittance be a single-compartment, self-erasing, solution-phase device according to the present invention, which has two planar, parallel, spaced-apart sides, at least one of which is transparent (and through which light reflected by the mirror from the reflecting means passes prior to and after reflecting from the reflecting means) and the other of which, if not transparent, has a highly reflecting layer, which serves as the reflecting means of the mirror, adhered to its side opposite the side in contact with the solution.

Construction and operation of single-compartment, self-erasing, solution-phase electrochromic devices, essentially the same as those of the present invention but having different solutions of reversibly variable transmittance, are known in the art. See Manos, Bredfeldt et al., Shattuck and Sincerbox, and Clecak et al., supra.

In FIG. 1, the basic structural elements of a typical device of the invention are illustrated in an exploded view. These elements include two planar electrode-bearing sides or walls, 100 and 130, a spacing or separating layer, 11, which spaces apart and holds parallel the walls 100 and 130 in an assembled device, and surrounds a space or volume, 12. Volume 12 is defined, in an assembled device, by electrode layers, 10A and 13A, of the electrode-bearing walls 100 and 130, respectively, as well as the four inside walls, 11A, 11B, 11C and 11D, of layer 11 (In FIG. 1, inside walls 11B and 11C are hidden from view.). In an assembled device, volume 12 is filled (or nearly filled, in case room is left for expansion with temperature increase) with a solution according to the invention, which has reversibly variable transmittance in operation of the device. The solution in volume 12 is in contact with both electrode layers 10A and 13A during operation of the device.

Usually, and preferably, in an assembled device, walls 100 and 130, including electrode layers 10A and 13A, and the layers 10 and 13, respectively, of the solid material to which the electrode layers adhere, are planar and parallel. By "planar" and "parallel" in the present specification are meant planar and parallel, respectively, within normal tolerance limits, as understood in the art, taking account of possible slight variations arising from slight deviation in uniformity of thickness at different points (e.g., of each of layers 11, 10, 10A, 13 and 13A in the Figures), flexibility of materials, and the like.

However, it is to be understood that, as long as volume 12 can be sealed after being filled (or nearly filled) with solution, electrode-bearing layers 100 and 130 can be other than planar and can be spaced so that their inner, electrode layers are other than equidistant at each point (provided the electrode layers do not come into contact with each other). Further, although in the preferred devices layer 100 and layer 130 will be made from the same materials, having electrode layers (10A, 13A) of the same thickness and same material, having solid material layers (10, 13) of the same thickness and same material, and otherwise be essentially the same, it is not necessary that this be the case. The electrode layers, like the solid material layers, can be of different materials and different thicknesses.

In typical devices of the invention, solid material layers, 10 and 13, of walls 100 and 130, respectively, will be made of clear glass or clear plastic, between 0.05 cm and 1 cm thick, which are suitable for coating with layers of electrically conducting material, to form electrode layers 10A and 13A. Layers 10 and 13 can, however, be made of any material which is transparent and to which an electrically conducting material can be affixed to form electrode layers.

Electrode layers, 10A and 13A, can be made of any electrically conducting material that can be adhered in a layer to the material of solid material layers, 10 and 13, respectively, and that is essentially chemically inert to the solutions of reversibly variable transmittance that are employed in devices of the invention. Suitable materials for the electrode layers are thin, transparent layers of gold, tin oxide, ruthenium oxide, cadmium stannate, and indium-doped tin oxide ("ITO"), or thin, highly reflective layers of materials such as rhodium, or Inconel. Preferred is ITO. Methods of applying the electrically conducting material to the solid material, of layers 10 and 13, to form suitable electrode layers are known in the art.

Figure 2:
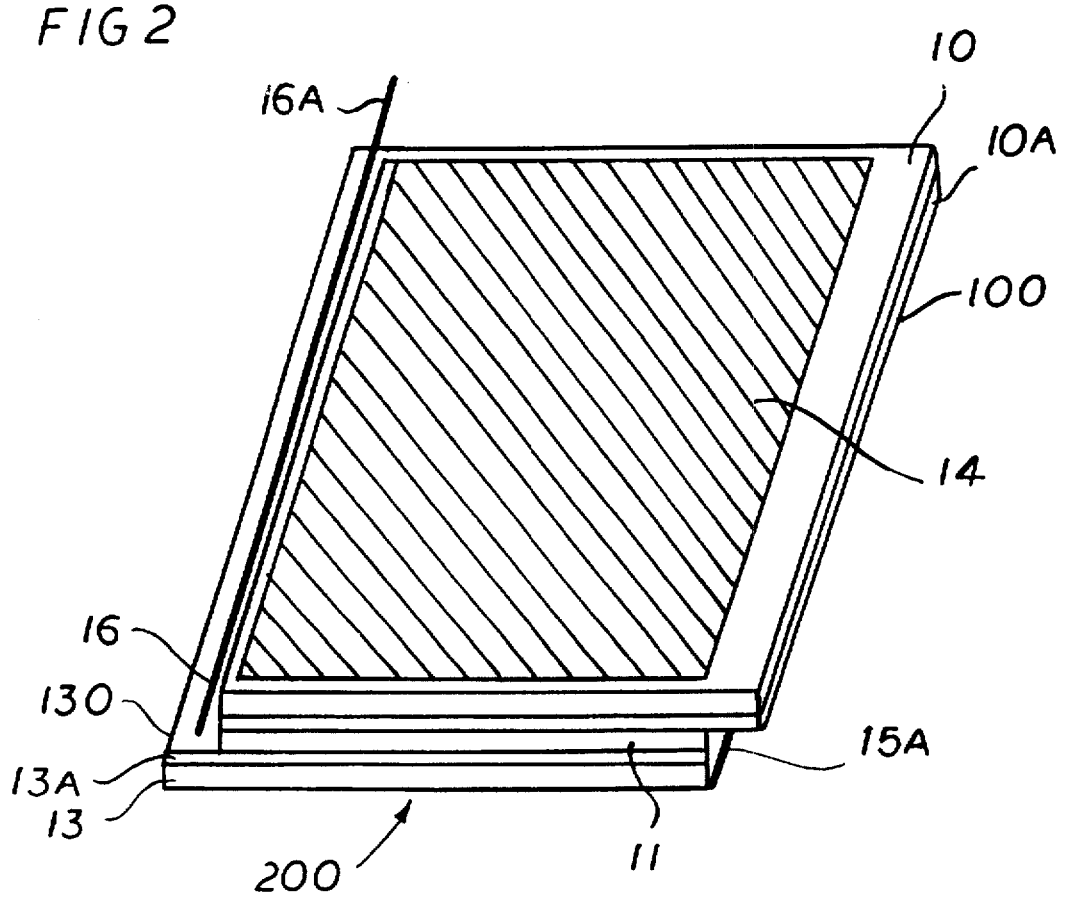
FIG. 2 illustrates schematically a partially assembled device, 200, according to the invention.

Preferably, as illustrated in FIGS. 1 and 2, the electrode layer will cover the entire surface of a solid material layer, over the volume 12 and spacer 11 as well as on an extension of the solid material layer beyond an outside wall of spacer 11 (i.e., with reference to FIG. 1, a wall of spacer 11 opposite wall 11A, 11B, 11C or 11D). The electrode layer will preferably have a thickness that is as uniform as possible over the entire surface of the solid material layer to which it is affixed the thickness of the electrode layer will preferably be such that it has a sheet resistance of less than 100 ohms per square and, more preferably, less than 40 ohms per square. It is, however, not necessary that the electrode layer cover the entire solution volume of a device of the invention or extend outside the spacer which holds apart electrode-bearing walls of the device, as long as electrical contact can be made with the layer and, in operating the device, solution in the solution space is in contact with the electrode layer. Further, it is not required that the electrode layer have uniform thickness or that it have a sheet resistance less than 100 ohms per square.

It is also possible, in a device of the invention, to have one or both electrodes separate from solid material layers, such as 10 and 13 in the Figures. With reference to FIG. 1, in place of electrode layers 10A and 13A, electrode strips could, for example, be situated along and parallel to sides 11B and 11D. Alternatively, one of electrode layers 10A and 13A could be replaced with an electrode plate or strip parallel to but not adhered to solid material layer 10 or 13, respectively. If the electrodes are separate from the solid material layers, the electrodes as well as the solid material layers are of material that is essentially chemically inert to solutions of the invention. In such devices, glass is a suitable material for the solid material layers and rhodium or platinum are suitable as electrodes.

The devices of the invention reversibly modulate the intensity of light that enters and leaves the device. Thus, in a device of the invention, at least part of at least one wall of the solution space is transparent to light of a range of wavelengths which includes at least a part of the range of wavelengths over which the transmittance of the solution of the invention in the solution space is reversibly varied in operation of the device. In the typical device, the entire area of both walls of the solution space will be transparent to light of all wavelengths in at least the visible range.

In a preferred variable transmittance light filter according to the invention, the device of reversibly variable transmittance will be a device according to the invention wherein both walls of the solution space (e.g., 100 and 130 in FIG. 1) are transparent to visible light of all wavelengths.

To prepare a variable reflectance mirror according to the invention, a highly reflecting layer, such as of silver, can be applied to the outside (i.e., the side opposite the solution) of one of the transparent walls of the solution volume of a device according to the invention, wherein, but for the reflecting layer, both walls of the solution space would be transparent. Alternatively, a variable reflectance mirror can be made by employing for one of the electrode layers defining the solution space in a device, a highly reflecting, electrically conductive material such as rhodium or Inconel.

As described further below, transparent walls of a device of the invention, defining the solution volume, can be joined, bonded or laminated to plates of glass or plastic, mirrors, and the like to make variable transmittance light filters and variable reflectance mirrors according to the invention wherein variable transmittance to light is provided by a device of the invention.

In the present specification, "transparent" to light of a range of wavelengths means that at least some light, of all wavelengths in the range, passes through, instead of being absorbed or reflected. Use of the word "transparent" without qualification means transparency to light of a range of wavelengths which includes at least all wavelengths in the visible range (wavelength from 4200Å to 7000Å). Typically, and as a practical matter, a transparent wall of the solution volume of a device of the invention will allow at least about 90% of the light, at all wavelengths in the visible range, that is incident on it to pass through, rather than be reflected or absorbed.

In contrast, a "highly reflecting" surface, within the meaning of the present specification, is one that reflects, rather than transmits or absorbs, at least about 50%, and more typically at least about 70%, of light of all wavelengths in an identified range. If used without qualification, a surface that is "high reflecting" is one that is so to light of all wavelengths at least in the visible range.

The spacer, denoted as 11 in the Figures, is electrically insulating and is made of a combination of a sealing material, such as epoxy resin, silicones, rubber cement, low melting glass, certain plastics, paraffin wax, or the like, with a spacing material such as small glass beads, nylon monofilament, MYLAR® strips, polystyrene beads or the like. As indicated above, the spacer is preferably of substantially uniform thickness so that the two walls defining the solution space in a device can be held essentially parallel to each other. Although shown schematically as planar in FIG. 1, the inside edges 11A, 11B, 11C and 11D of the spacer, and the outside edges opposite the inside edges, are in reality curved or rough edged. This curvature or roughness will be clear from the manner by which a typical device is assembled: by placing strips of a (highly viscous) mixture, of sealing material with spacing material, around an area on the inside (i.e., electrode layer bearing side) of one wall of a device and then pressing the other wall of the device, with its inside (i.e., electrode-bearing side) wall facing the inside of the first wall, against the strips until both walls contact the separating means. This pressing squeezes excess sealing material in the strips from the strips and causes the outside and inside edges of the strips to be curved or uneven. In the devices of the invention, the separating material in the spacer holds the inside (i.e., electrode-bearing) surfaces of walls between about 0.0025 to about 0.05 cm apart. A preferred spacer is a combination of glass beads with epoxy resin sealant.

The electrodes of a device of the invention are connected to, or capable of being connected to, a DC power source, whereby an electrical potential can be impressed between the electrodes and across the solution in a device. In the device illustrated schematically in FIG. 2, a preferred arrangement for connecting the electrodes to a power source is illustrated. In this arrangement, the two electrode-bearing walls are displaced in opposite directions, laterally from but parallel to the solution space, in order to provide an exposed strip of each of the electrode surfaces. To each of these exposed strips is adhered, so as to be in electrical contact with the strip along nearly its entire exposed length, an electrically conductive strip or wire, such as a copper, aluminum or silver strip or wire. One such strip, 16, is shown in its entirety in FIG. 2 and in cross-section in FIGS. 3 and 4. Only the lead or extension, 15A, of the other strip 15 of the device of FIG. 2 is seen in FIG. 2. Strip 15 is seen in cross-section in FIGS. 3 and 4. Like strip 16 affixed to electrode-layer 13A, strip 15 is affixed to electrode layer 10A along essentially the entire length of the overhang of the electrode layer. Although any means known in the art can be employed to secure the wire or strip in electrical contact with the electrode surface, such as clamping, soldering or securing with a conductive adhesive, a preferred means is to use a conductive epoxy, such as standard silver epoxy. The strips or wires affixed to the electrode surfaces have leads or extensions, illustrated by 15A and 16A in FIG. 2 beyond the ends of the electrode surfaces. Connection to a suitable power source is effected by standard electrical connection from the power source to these leads or extensions.

Assembly of a device of the invention can be carried out as understood in the art. See Manos, supra. A preferred method for assembling a device is as follows:

A strip of spacer material, consisting of a separating material, such as glass beads, mixed with a sealing material, such as insulating epoxy, is deposited on one surface of the device (on the electrode surface thereof, in the preferred case wherein the surface of the device is a planar piece of solid material, such as glass, to which is affixed or adhered a layer of electrically conducting material to serve as an electrode) to outline a cross-sectional area, of desired size and shape, for the solution volume. The solution volume is then formed by placing the other surface of the device over the strip of spacer material, so that the electrode layers of the surfaces face each other, and then applying pressure to the two surfaces to cause them to approach each other until they are separated substantially only by the separating material in the spacer. If the solution used with the device is to be thickened by combination with a thickener, such as acrylic sheet material, as derived from LUCITE L®, a solution of the thickener in a volatile solvent such as dichloroethane, acetone or methyl ethyl ketone is conveniently painted or sprayed on the entire area outlined by the spacer on the first wall, and the solvent allowed to evaporate, prior to application of the second wall. After the assembly process, and prior to filling with a solution, the sealing material of the spacer is allowed to cure, if necessary, to become inert to the solution, such curing is necessary when the solvent of the solution is propylene carbonate and the sealing material is insulating epoxy.

The shape of the solution volume, viewed in cross-section through the electrode-bearing walls, is not constrained to be square or rectangular. It can be circular, elliptical, polygonal, in the shape of a letter or numeral, or any desired shape.

One of the walls of a device of the invention has bored therein (prior to assembly) two small holes located, in the assembled device, over and near the edge of, the solution volume (e.g., with reference to FIG. 1, one near inside wall 11A and the other near inside wall 11B). The device is filled with solution of the invention through these holes by passing solution in through one of them while allowing air to escape out the other. After the filling, the two holes are sealed first with a conventional thermoplastic material inert to the solution and secondarily with a sealant such as, for example, insulating epoxy.

Then conducting wires or strips, usually copper strips, are adhered, usually with a conducting epoxy such as a standard silver epoxy, to the exposed portions of both electrode surfaces. Finally, employing the sealing material used in the spacer, the wires or strips, except for the leads or projections thereof through which contact with a power source is made, are sealed over, as is the entire periphery of the device, i.e., the outside of the rim or sides which include the spacer.

For solvent in a solution of the invention, any compound, or mixture of compounds, can be employed, which is liquid over the range of temperatures, at which the solution of the invention is to be used as the medium of reversibly variable transmittance in a device of the invention, and which is known to be useful as a solvent in the electrochemical arts. As a practical matter, for convenience in preparing the solutions and because devices of the invention usually will be operated over a range of temperatures which includes room temperature, a solvent will be liquid over at least the range between 20° C. and 27° C. (i.e., room temperature). Further, it is preferred, for the sake of stability of devices of the invention, that the solvent of solution of the invention not undergo electrolysis or be involved in other, irreversible chemical reactions, during storage or normal operation of a device. Suitable as solvents are water, methanol, ethanol, acetonitrile, N,N-dimethylformamide, dimethylsulfoxide, acetone, methyl ethyl ketone, cyclopentanone, and cyclic esters, including propylene carbonate, ethylene carbonate, β-propiolactone, β-butyrolactone, gamma-butyrolactone, gamma-valerolactone, delta-valerolactone or homogeneous (i.e., single-phase) mixtures of them. It is preferred that the solvents be substantially free of dissolved oxygen and, but for water, be anhydrous. Preferred solvents are the cyclic esters or combinations thereof. Most preferred is propylene carbonate.

In a solution of the invention, there is at least one cathodic electrochromic compound, at a concentration at 25° C. of at least $10^{-4}$ M up to its solubility, but more usually between about 0.01 M and 0.1 M, which, in the solvent of the solution, as determined by standard voltammographic techniques at an inert electrode at room temperature, has at least two chemically reversible (i.e., not necessarily kinetically reversible, as understood in the electrochemical arts) reduction waves, the first of these reductions being accompanied by an increase in the extinction coefficient of the cathodic compound at at least one wavelength in the visible range.

Further, in a solution of the invention, there is at least one anodic electrochromic compound, at a concentration at 25° C. of at least $10^{-4}$ M up to its solubility, but more usually between about 0.01 M and 0.1 M, which, in the solvent of the solution, as determined by standard voltammographic techniques at an inert electrode at room temperature, has at least two chemically reversible (as understood in the electrochemical arts) oxidation waves, the first of these oxidations being accompanied by an increase in the extinction coefficient of the anodic compound at at least one wavelength in the visible range.

Usually it is intended that, upon application of a potential difference across the solution between the electrodes of a device of the invention, the solution change from clear to dark or change color. Thus, it is desirable that the first chemically reversible reduction of a cathodic electrochromic compound or first chemically reversible oxidation of an anodic electrochromic compound employed in a solution of the invention be accompanied by an increase in extinction coefficient, in the solvent of the solution at room temperature, by a factor of at least about $10^2$ to at least about $10^3$ cm$^{-1}$ M$^{-1}$ at at least one wavelength in the visible range.

Among the cathodic electrochromic compounds suitable for solutions of the invention are the known compounds of Formula II (viologens)

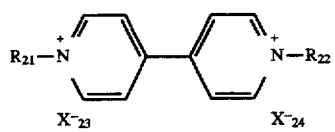

wherein $R_{21}$ and $R_{22}$ are the same or different and are each selected from alkyl of 1 to 10 carbon atoms, phenyl optionally substituted at any one position with chloride, bromide, iodide, cyano, or an alkyl group of 1 to 4 carbon atoms, and benzyl, wherein the phenyl group is optionally substituted at any one position with chloride, bromide, iodide, cyano, or an alkyl group of 1 to 4 carbon atoms; and wherein $X^-_{23}$ and $X^-_{24}$ are the same or different and are each selected from chloride, bromide, iodide, BF$^-_4$, PF$^-_6$, AsF$^-_6$, ClO$^-_4$ and NO$^-_3$; and the known compounds of Formula III

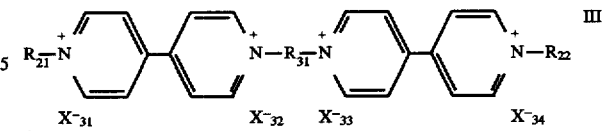

wherein $R_{21}$ and $R_{22}$ are the same or different and are defined as above for the compound of Formula II, $R_{31}$ is alkylene of 1 to 10 carbon atoms, and $X^-_{31}$, $X_{32}$, $X^-_{33}$ and $X^-_{34}$ are the same or different and each selected from chloride, bromide, iodide, BF$^-_4$, PF$^-_6$, AsF$^-_6$, ClO$^-_4$ and NO$^-_3$.

The preferred compounds of Formulas II and III are those wherein all of the anions are the same and are ClO$_4$ or BF$^-_4$. Most preferred is BF$^-_4$. The preferred cations of compounds of Formula II are those wherein $R_{21}$ and $R_{22}$ are the same and are benzyl, phenyl or n-heptyl; most preferred is benzyl. The most preferred cation of compounds of Formula III is that wherein $R_{31}$ is —(CH$_2$)$_4$— and $R_{21}$ and $R_{22}$ are the same and are benzyl (i.e., tetramethylene bis[4(1-benzyl-pyridine-4'-yl)pyridinium].

Among the anodic electrochromic compounds suitable for solutions of the invention are the known compounds of Formula IV

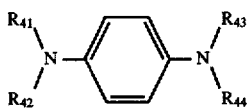

wherein $R_{41}$, $R_{42}$, $R_{43}$ and $R_{44}$ are the same or different and are each selected from hydrogen, alkyl of 1 to 10 carbon atoms, phenyl optionally substituted at any one position with chloride, bromide, iodide, cyano, or an alkyl group of 1 to 4 carbon atoms, and benzyl, wherein the phenyl moiety is optionally substituted at any one position with chloride, bromide, iodide, cyano, or an alkyl group of 1 to 4 carbon atoms;

the known compounds of Formula V

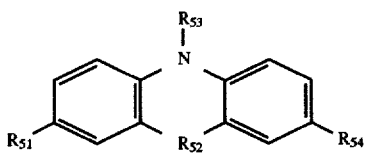

wherein $R_{51}$ and $R_{54}$ are the same or different and are each selected from hydrogen and dialkylamino, wherein the alkyl groups are the same or different and are each of 1 to 6 carbon atoms; $R_{52}$ is oxygen, sulfur or $NR_{55}$, wherein $R_{55}$ is the same as or different from $R_{53}$ and both $R_{55}$ and $R_{53}$ are selected from hydrogen, alkyl of 1 to 10 carbon atoms, phenyl optionally substituted at any one position with chloride, bromide, iodide, cyano, or alkyl of 1 to 4 carbon atoms, or benzyl, optionally substituted at any one position of the phenyl group with chloride, bromide, iodide, cyano, or alkyl of 1 to 4 carbon atoms;

the known compounds of Formula VI

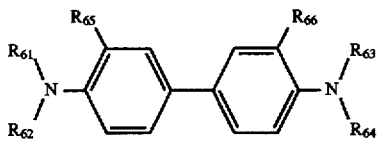

wherein $R_{61}$, $R_{62}$, $R_{63}$ and $R_{64}$ are the same or different and are each selected from alkyl of 1 to 10 carbon atoms or phenyl; and $R_{65}$ and $R_{66}$ are the same or different and are each selected from hydrogen or alkyl of 1 to 10 carbon atoms, provided that both $R_{65}$ and $R_{66}$ are hydrogen or both are alkyl, and if $R_{65}$ and $R_{66}$ are both hydrogen, not more than one of $R_{61}$ and $R_{62}$ is hydrogen and not more than one of $R_{63}$ and $R_{64}$ is hydrogen;

the known compound of Formula VIII (tetrathiafulvalene)

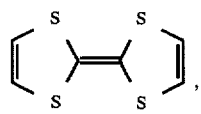

Also suitable as an anodic compound in solutions of the invention is a novel compound of the invention, of Formula VII

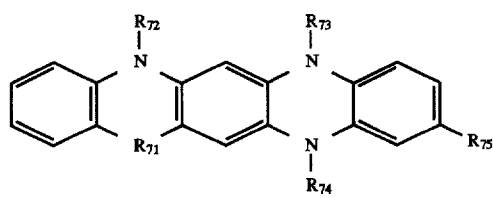

wherein $R_{71}$ is oxygen or sulfur, $R_{75}$ is hydrogen or dialkylamino, wherein the alkyl groups are the same or different and are each selected from alkyl of 1 to 6 carbon atoms, and $R_{72}$, $R_{73}$ and $R_{74}$ are the same or different and are each selected from hydrogen, alkyl of 1 to 6 carbon atoms, phenyl, optionally substituted at any one position with an alkyl group of 1 to 6 carbon atoms, and benzyl, optionally substituted at any one position of the phenyl group with an alkyl group of 1 to 6 carbon atoms.

Most preferred among the compounds of Formula VII is that wherein $R_{71}$ is oxygen, $R_{75}$ is hydrogen and $R_{72}$, $R_{73}$ and $R_{74}$ are all methyl.

Preferred among the anodic electrochromic compounds for solutions of the invention are those of Formulas IV and V. More preferred are those of Formula IV wherein $R_{41}$, $R_{42}$, $R_{43}$ and $R_{44}$ are the same and are methyl or phenyl, and those of Formula V wherein $R_{51}$ and $R_{54}$ are hydrogen, $R_{52}$ is the same as N—$R_{53}$ and $R_{53}$ is methyl or phenyl. Most preferred are N,N,N',N'-tetramethyl-1,4-phenylene diamine and 5,10-dihydro-5,10-dimethylphenazine.

Preparation of the novel compounds of the invention, of Formula VII, follows known procedures of Gilman and Dietrick (J. Amer. Chem. Soc. 79, 6178 (1957)), beginning with the known compound of Formula XX

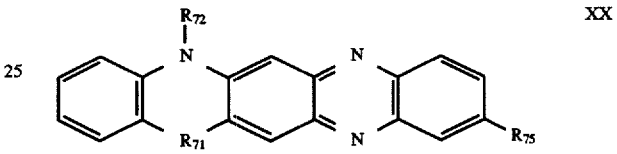

wherein $R_{71}$, $R_{72}$ and $R_{75}$ are as defined above for compounds of Formula VII, to form the potassium adduct of Formula XXI

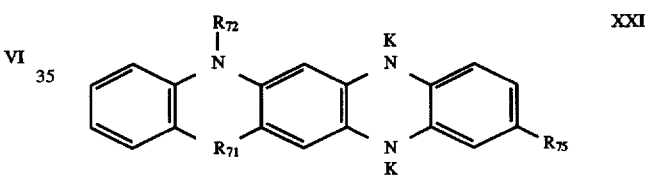

and then reacting the adduct with a mixture of compounds of Formula $R_{73}I$ and $R_{74}I$ where $R_{73}$ and $R_{74}$ are as defined above for the compound of Formula VII and can be the same, to yield the desired product after crystallization. This synthetic procedure is illustrated in Example XI, with the synthesis of the preferred N,N',N"-trimethyltriphenazinoxazine.

A solution of the invention will include inert, current-carrying electrolyte, if none of the cathodic electrochromic compounds and anodic electrochromic compounds, in their zero-potential equilibrium states in the solution, is ionic, and otherwise may optionally include such inert, current-carrying electrolyte. The inert, current-carrying electrolyte will, during normal operation of a device of the invention, carry current across the solution between the electrodes and, during storage or normal operation of a device, will not undergo electrolysis or other irreversible chemical reactions with other substances in the device so as to impair the stability of the device.

The inert, current-carrying electrolyte in a solution of the invention will consist of any combination of substances known in the art to be suitable for inert, current-carrying electrolyte (sometimes referred to in the art as "supporting electrolyte"). Such substances include alkali metal salts, tetraalkylammonium salts, and aluminum chloride and bromide. Preferred as cations in inert, current-carrying electrolyte in solutions of the invention are lithium, sodium, and tetraalkylammonium, wherein the alkyl groups are the same most preferred is tetra-n-butylammonium. Preferred as anions in inert, current-carrying electrolytes in solutions of the invention are chloride, $BF_4^-$ and $ClO_4^-$; most preferred in $BF_4^-$. The concentration of inert, current-carrying electrolyte, if present in the solution of the invention, will be between 0.005 M to 2 M at 25° C. More preferably, it will be between 0.05 M and 0.5 M at 25° C.

The solutions of the invention are for use as the variable transmittance medium in a single-compartment, self-erasing, solution-phase electrochromic device. Because the devices are "solution-phase", the concentrations of substances in the solution, for a device to be operated over a given temperature range with the potential applied across the solution not exceeding a given maximum, must be such that precipitation of substances from the solution does not occur, both at zero-potential equilibrium and during operation of a device, when cathodic electrochromic material(s) is (are) being reduced at the cathode and anodic electrochromic material(s) is (are) being oxidized at the anode. Generally, provided that, at zero-potential equilibrium at all temperatures in the range of intended use, all substances are present in the solution at concentrations below their solubilities, precipitation will not occur during operation of a device which includes the solution as the medium of reversibly variable transmittance.

The "self-erasing" property of devices of the invention means that, after a potential difference between the electrodes of a device is decreased or eliminated, the transmittance of the solution in the device will increase spontaneously, without need for reversal of the polarity of the electrodes, to a value characteristic of the new potential difference. The "self-erasing" feature of the devices of the present invention is provided by the spontaneous, apparently diffusion-limited, reactions of oxidized anodic compounds with reduced cathodic compounds to yield anodic compounds and cathodic compounds in their respective zero-potential equilibrium states.

It is important, in practical applications of the devices of the invention, that both decrease in transmittance of the solution of a device, that occurs when the potential difference between the electrodes is increased, and the increase is transmittance of the solution of a device, that occurs with self-erasing, occur sufficiently rapidly. It is generally advantageous that both decrease and increase in transmittance occur as rapidly as possible. Until the instant invention, cathodic and anodic compounds meeting the voltammographic and calorimetric criteria specified above, were not combined in a solution. It has not been realized in the art that, by having both cathodic and the anodic compounds in a single-compartment, solution-phase electrochromic device that undergo increases in absorbance in the wavelength range of interest, with reduction and oxidation, respectively, that the speed of transmittance decrease could be a speed acceptable for commercial application of such devices without causing commercial application-defeating loss in the speed of transmittance increase, by self-erasing, made possible by the solution-phase characteristic of the devices.

Further, for practical applications of devices of the invention, it is important that the solutions in the devices be stable, both during periods when the device is not being operated and during cycling (i.e., when the potential between the electrodes of a device is cycled between zero or a low value to a higher value and back and, as a result, the transmittance of the solution in the device varies reversibly between higher and lower values). Lack of stability is indicated by an increase in absorbance of white light, or light of wavelengths at which absorbance is varied with the device, passing through the device, including the solution therein, when the solution is at zero-potential equilibrium, i.e., equilibrium with no potential difference between the electrodes of the device.

A problem preventing commercial application of single-compartment, self-erasing, solution-phase electrochromic devices has been the lack of stability of the solutions of variable transmittance employed with them. While the reasons for this instability of prior art devices are not entirely clear, they might be related to the chemical instability, and high reactivity, with solvent and other materials, of either or both of the anodic and cathodic compounds, in their oxidized and reduced states, respectively, that have been used in prior art solutions. The present invention has solved this problem with discovery that, with cathodic and anodic electrochromic compounds satisfying the above-specified voltammographic criteria, a property of the solutions of the invention is exceedingly and unexpectedly high stability, particularly stability to cycling.

It has been found that the stability of the solutions of the invention is further enhanced by minimizing in the solutions the concentration of oxygen and, if the solvent is non-aqueous, water. Thus, optionally but preferably, a device of the invention is flushed with dry nitrogen or other inert gas prior to being filled with solution. Standard techniques are employed to reduce the concentrations of oxygen and, if solvent is non-aqueous, water, in solvent and solutes used to prepare solutions and to minimize contamination of solutions with oxygen and water prior to filling the devices with the solutions and sealing the filled devices. For example, dry nitrogen can be bubbled through solutions prior to filling to reduce oxygen concentration. Solvent can be treated by passing over a dessicant, such as activated alumina, to reduce water contamination, prior to being used to prepare a solution. In addition, solutes (electrochromic compounds; inert, current-carrying electrolyte) can be dried prior to use to prepare solutions by heating to about 110° C. Alternatively, prepared solutions can be passed through a dessicant, such as activated alumina, prior to filling a device with them.

Other than any of the aforementioned measures, that might be taken to reduce the concentrations of oxygen and water in solutions of the invention, solutions of the invention are prepared by standard methods, usually at room temperature, by simply dissolving the appropriate amounts of solutes in the solvent to achieve the desired concentrations.

Certain advantages are realized by employing thickened or gelled solutions as the media of reversibly variable transmittance in devices of the invention. As described supra and further below, it has been discovered in connection with the present invention that segregation is a problem with single-compartment, self-erasing, solution-phase electrochromic devices when they are operated continuously for long periods. Gelling or thickening the solutions of the invention reduces the significance of the segregation problem by reducing the component of the segregation that is due to natural convection.

Another advantage realized by using gelled or thickened solutions in the devices of the invention relates to convenience and safety. If a device should be opened, as by breaking one of the transparent sides or otherwise, a gelled or thickened solution would flow much more slowly than a non-gelled or non-thickened one and, consequently, the ease of cleaning up the solution would be increased and the risk of persons' contacting any noxious or harmful substances that might be present in the solution would be reduced. In devices, wherein the transparent sides or other elements might shatter or splinter during breakage, a gelled or thickened solution would tend to hold the broken pieces in place and thereby reduce the risk of injury that might occur if the device broke apart.

The terms "thicken" and "gel" are used interchangeably in the instant specification and refer to the increase in viscosity of a solution that results from combining it with certain substances, whether or not a true gel is formed in the process. Any substance which can thicken a solution, without reacting to form covalent bonds with solvent, inert, current-carrying electrolyte or anodic or cathodic compounds therein, can be employed to thicken or gel a solution of the invention. The desired amount of thickening or gelling substance can simply be combined with solution, just prior to filling a device, provided there is sufficient time for such filling prior to the solution's becoming too viscous. Alternatively, the desired amount of thickening or gelling substance can be placed into a device before or after introduction of solution and the mixture with solution be accomplished in situ in the solution space of the device; an example of this method, in which the thickener is introduced before the solution, is provided in Example X.

The concentration of thickening or gelling substance employed to prepare a thickened or gelled solution of the invention will vary, depending on a number of factors, as understood by the skilled. These factors include the thickening or gelling substance employed, the solvent employed and the desired viscosity of the thickened or gelled solution. With the preferred solvent, propylene carbonate, and the preferred thickener for this solvent, the composition obtained by dissolving the acrylic sheet material sold under the trademark LUCITE L, in an organic solvent such as acetone, methyl ethyl ketone or dichloroethane, the concentration of thickener in solution will be between about 3% (w/w) and about 30% (w/w), preferably between about 5% (w/w) to about 25% (w/w), and most preferably between about 7% (w/w) and about 15% (w/w).

Manos, supra, lists certain other thickeners which can be employed to make thickened or gelled solutions of the invention. It has been found in connection with this invention, with propylene carbonate solvent, that the composition, obtained by dissolving the acrylic sheet material sold under the trademark PLEXIGLAS in an organic solvent such as acetone, methyl ethyl ketone, or dichloroethane, can also be used for the thickening.

The preferred thickener is obtained by mixing a solvent, such as dichloroethane (1,2-dichloroethane, 1,1-dichloroethane or mixtures of the 1,1 and 1,2 isomers) with the commercially available acrylic sheet material, LUCITE L®, separating the resulting solution from any residue, and, finally, allowing the solvent to evaporate. The residue left after the solvent evaporates is the "acrylic sheet material thickener."

It has been discovered unexpectedly, in connection with the instant invention, that using this preferred thickener is unusually convenient and exceptionally suitable for constructing devices of the invention which employ propylene carbonate solutions as media of reversibly variable transmittance. This convenience and suitability is due to the facts, illustrated in Example X, that a quantity of thickener can be placed in a device by simply painting or spraying the solution of the thickener on the electrode-bearing side of a wall of the device and then allowing the solvent to evaporate before assembling the device and that the thickener inside the device is spontaneously taken up by and thickens a propylene carbonate solution of the invention, after the assembled device is filled with the solution in the usual manner.

An unexpected and highly desirable property, discovered in connection with the instant invention, of solutions of the invention thickened with the preferred acrylic sheet material thickener is that the time required for coloring of a device wherein such a solution is employed as the medium of reversibly variable transmittance is not significantly increased over the time required for coloring in a device which is the same but for having no thickener in the solution. Thus, with such thickener, the aforementioned advantages of using a thickened solution as the medium of reversibly variable transmittance in a device of the invention can be realized without significant effect on the advantage, of rapid coloring, of devices which employ non-thickened solutions of the invention as media of reversibly variable transmittance.

To be operated, a device of the invention is connected to a power source capable of establishing a potential difference of constant polarity between the electrodes of the device. Referring to FIGS. 1 and 2, this connection is effected through leads 15A and 16A of the electrically conducting wires or strips affixed to the electrode layers of the walls of the device so as to be in electrically conductive contact with the electrode layers. The power source can be any AC or DC power source known in the art; however, if an AC source, control elements, such as diodes, are placed between the power source and the electrodes of the device to insure that the potential difference between the electrodes does not change in polarity with variations in polarity of the potential from the source. Suitable DC power sources are storage batteries, such as automobile batteries and dry cell batteries. The power from the power source delivered to the electrodes of the device is controlled by any means known in the art so that the potential across the solution between the electrodes of the device does not exceed the potential difference at which irreversible reactions, such as electrolysis of solvent, reduction or oxidation of inert, current-carrying electrolyte, unimolecular degradation reactions of electrochromic compounds and the like, occur. Preferably, to make use of the gray-scaling capability of the devices of the invention, the control of power delivered to the electrodes of the device will be such that the potential can be varied, over a range from about 0.1 volt to a potential somewhat below that at which irreversible reactions occur to a significant extent in the device, but held constant at any desired potential in this range. There will also be a switching means associated with the power source so that the potential between the electrodes of the device can be reduced to zero, by open-circuiting or short-circuiting. Because, in certain instances, the additional speed in self-erasing that can be achieved by applying a potential for a brief period (e.g., about 0.5 to about 5 seconds) to the electrodes, with polarity reversed from that during decreasing transmittance, the switch means may also include means for accomplishing such reversals. The means for controlling the potential delivered to the electrodes and the switching means can be either manually or automatically operated.

In order for the electrochromic compounds in the solutions of the invention to be oxidized and reduced, and thereby cause decrease in transmittance of the solution, the potential difference between the electrodes must be high enough to cause a current to flow across the solution between the electrodes. A potential difference between about 0.3 volts and about 0.5 volts is usually adequate to cause current to flow and solution of the invention to begin to darken or change color.

The extent of darkening at steady state in a particular device of the invention will depend on the potential difference between the electrodes; because of this property the devices of the invention are useful as "gray-scale" devices.

The maximum potential that can be applied between the electrodes of a device without impairing the stability of the solution will, as the skilled understand, depend on a number of factors, such as the potential at which electrolysis of solvent occurs and potentials at which degradative reactions of electrochromic compounds occur. Devices of the invention wherein water is solvent in the solution will generally be operated at less than about 1.4 volts to avoid electrolysis of water. The devices of the present invention with cyclic ester solvents can, in some cases, be operated at a potential difference as high as about 4 volts across the solution layer. Generally, however, the potential across the solution layer in devices of the invention is kept below 2 volts.

The skilled will understand that, at steady state at a given potential across the solution layer of a device of the invention, cathodic electrochromic compounds are being reduced and anodic electrochromic compounds are being oxidized continuously at the electrodes while, at the same time and at the same rate at which electrochemical oxidation and reduction are occurring, reduced cathodic compounds are being oxidized back, and oxidized anodic compounds reduced back, to their zero-potential equilibrium forms by reaction of reduced cathodic with oxidized anodic compounds. The rate at which the steady-state is achieved, at a given potential across the solution of a device, is dependent on the current across the solution at the potential. This current is generally not regarded as an independent variable in operation of the devices, as it depends on other factors which are independently varied, such as the conductivity of the solution in the device (which in turn depends on solution composition, including composition of inert, current-carrying electrolyte), and the potential across the solution. However, the currents that flow during normal device operation are typically in the range of 0.1 to 20 milliamperes per square centimeter of cathode or anode area in contact with solution layer.

As indicated, supra, a problem that has been discovered in connection with the present invention is that segregation occurs in single-compartment, self-erasing, solution-phase electrochromic devices that are operated continuously (i.e., held at non-zero potential) for long periods, longer than about 20 minutes. This segregation appears to be similar to the segregation that is encountered in operation of large scale electrochemical cells. Thus, the segregation found in devices of the instant invention has a component due to migration of charged electrochromic compounds in electrical potential gradients in the solution layer of a device and a component due to natural convection, which arises from different local densities, one higher and one lower than bulk solution density, around oxidized anodic and reduced cathodic molecules.

Segregation in devices of the invention is preferably avoided because it gives rise to annoying color separation in the solution layer of devices of the invention and slows the rate at which the devices self-erase.

As indicated, supra, one method for reducing at least the natural convection component of segregation in devices of the invention is to employ a thickened or gelled solution of the invention as the medium of reversibly variable transmittance.

It has also been found in connection with the invention that segregation can be substantially eliminated in a device of the invention by (a) employing in the device a solution of the invention which (i) has concentrations of cathodic and anodic electrochromic compounds at the lower end of the concentration range that is acceptable for achieving sufficient reduction of transmittance in the solution for the uses in which the device is to be employed, and (ii) has a concentration of current-carrying electrolyte which is at least twice and preferably at least ten times the higher of the total concentration of anodic or total concentration of cathodic compounds and (b) with reference to FIG. 2, orienting the device so that one of the conducting strips or wires (16 and the strip or wire (not shown) of which lead 15A is an extension) is higher (i.e., further from the surface of the Earth) than the other and, in applying a potential to the device, to decrease or maintain below the zero-potential equilibrium value the transmittance of the solution in the device, placing the higher conducting strip or wire at the higher potential (so that the electrode to which it is attached is the anode).

For example, when oriented as just described, devices of the invention which have as medium of variable transmittance the solution described in Example XII, when operated continuously at 1.0 volts for 24 hours show no appreciable segregation.

Figure 3:
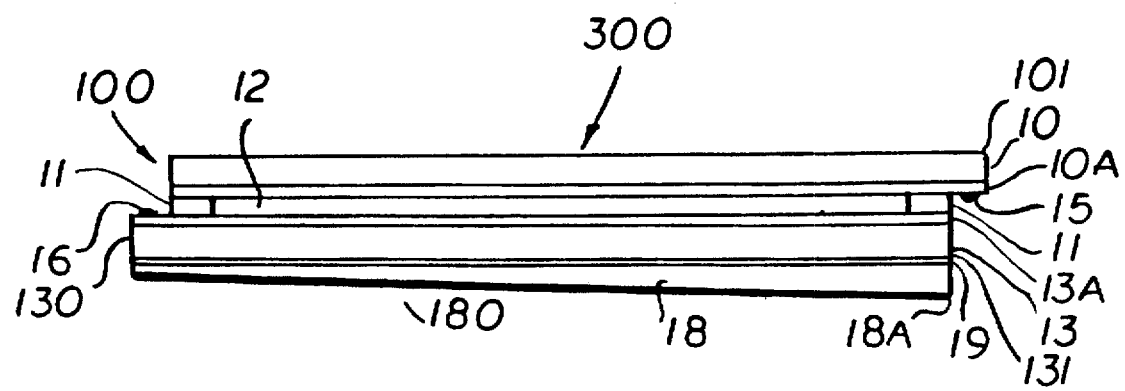
FIG. 3 illustrates schematically a view of a cross-section of a partially assembled, improved variable reflectance mirror, 300, according to the invention, wherein the reflecting means is the highly reflective layer 18A of a prism-shaped mirror, 180, laminated to surface 131 of one transparent, electrode-bearing side, 130, of a variable transmittance device according to the invention.
Figure 4:
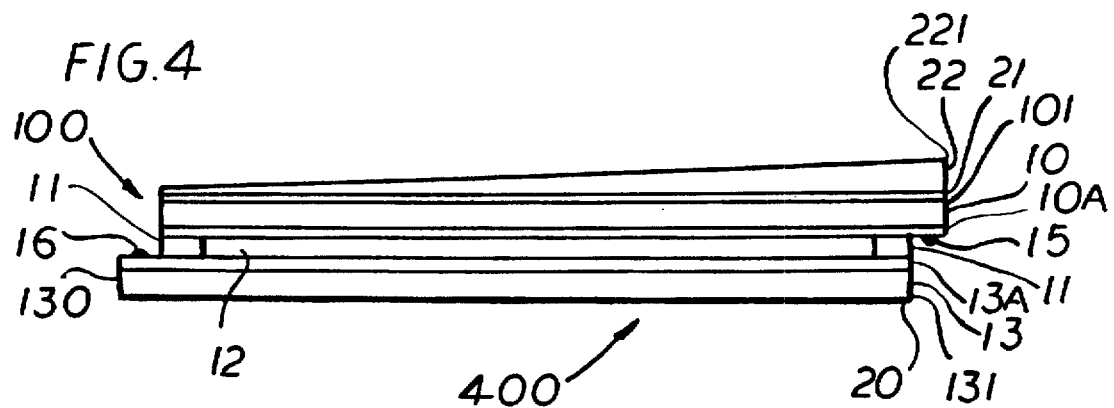
FIG. 4 illustrates schematically a view of a cross-section of a partially assembled, improved variable reflectance mirror, 400, according to the invention, wherein the reflecting means is a high reflectance layer, 20, on one electrode-bearing side, 130, of a variable transmittance device according to the invention and a transparent prism-shaped object, 22, is laminated to the surface 101 of the other electrode-bearing side, 100, of the variable transmittance device according to the invention.

In its final aspect, the instant invention relates to improved variable reflectance mirrors, preferred embodiments of which are illustrated schematically, in cross-sectional views, in mirrors 300 and 400 of FIGS. 3 and 4, respectively. As described, supra, the improvement in these mirrors arises from the positioning of the planar reflecting means, shown as 18A in FIG. 3 and 20 in FIG. 4, at a slight angle to the planar front surface of the mirror, which is shown as surface 101 of solid material layer 10 of wall 100 of mirror 300 in FIG. 3 and surface 221 of prism-shaped piece 22 of mirror 400 in FIG. 4. The front surface of the mirror is the surface through which light passes to enter and leave the mirror.

These mirrors of the invention comprise a device of reversibly variable transmittance through which light passes before and after reflecting from the reflecting means.

The device of reversibly variable transmittance is characterized by two planar, parallel, spaced-apart surfaces which are transparent to light of at least the wavelengths at which reflectance of the mirror is varied, and preferably to light of all wavelengths in at least the visible range, and between which is located a medium of absorbance which is reversibly variable by thermochromic, photochromic or electro-optic means in operation of the device. With reference to mirror 300 illustrated in FIG. 3 and mirror 400 illustrated in FIG. 4, these surfaces are surface 101 of solid material layer 10 and surface 131 of solid material layer 13.

Although, in mirrors 300 and 400 of FIGS. 3 and 4, respectively, the devices of reversibly variable transmittance, with surfaces 101 and 131, are electrochromic devices that are substantially the same as the device of the present invention illustrated in FIG. 2, the improved mirrors of the invention are not limited to having single-compartment, self-erasing, solution-phase electrochromic devices according to the instant invention as the device of reversibly variable transmittance. Any device of transmittance varied by thermochromic, photochromic or electro-optic means can be employed to vary the reflectance of an improved mirror of the invention, provided that the medium of variable transmittance is held in such device between two planar, parallel, spaced-apart surfaces which are transparent to light of at least the wavelengths at which the reflectance of the mirror is to be varied. A number of types of electro-optic devices, suitable for this purpose, are known (e.g., liquid crystal devices, dipolar suspension devices, electrophoretic devices, two-compartment electrochemichromic devices such as described by Kissa, supra).

In one type of improved, variable reflectance mirror according to the invention, which is illustrated by mirror 300 of FIG. 3, a prism-shaped mirror, 180, is laminated through a transparent laminating material, indicated by layer 19, to a surface, 131, of the device of reversibly variable transmittance. The prism-shaped mirror could be, for example, a conventional, prism-shaped mirror employed in rearview mirrors of automobiles. The prism-shaped mirror consists essentially of a prism-shaped piece, 18, of transparent solid material, such as of glass or a clear plastic, and a layer, 18A, of highly reflective material, such as silver, adhered to a surface of the solid material by any standard technique in the mirror-fabricating art so that a high fraction, preferably at least about 80%, of the light passing through the solid material and reaching the reflective material layer is reflected back through the solid material. The highly reflective surface of the prism-shaped mirror covers at least the entire cross-sectional area, illustrated by 14 in FIG. 2 but not shown in the cross-sectional view of FIG. 3, of reversibly variable transmittance of the device of reversibly variable transmittance of the improved mirror. Highly reflective layer 18A is the reflecting means of the improved mirror of the invention.

In another type of improved variable reflectance mirror according to the invention, similar to that illustrated in FIG. 3, the layer of laminating material is not present. Instead, the surface of the prism-shaped mirror which is not coated with a highly reflective layer is coated with an electrically conducting layer, to function as an electrode of the device of reversibly variable transmittance, and the prism-shaped mirror, with electrode layer, replaces wall 130 as one wall of said device.

In still another type of improved, variable reflectance mirror according to the invention, which is illustrated by mirror 400 of FIG. 4, the reflecting means is a layer, 20, of highly reflective material, such as silver, adhered, by any standard technique in the mirror-fabricating art, to surface 131 of the device of reversibly variable transmittance so that a high fraction, preferably at least about 70%, of the light passing through the device of reversibly variable transmittance that reaches the reflective material is reflected back through surface 131. Further, in the type of improved mirror illustrated by mirror 400 of FIG. 4, the surface, illustrated by 101, of the device of reversibly variable transmittance, that is parallel to and spaced-apart from surface 131, is laminated through a transparent laminating material, indicated by layer 21, to a prism-shaped piece, 2, of transparent solid material, such as glass or clear plastic, one surface, 221, of which is the front surface of the improved mirror through which light reflected by reflecting means 20 enters and leaves the mirror. The highly reflecting layer 20 and prism-shaped piece 22 cover at least the entire cross-sectional area, illustrated by 14 in FIG. 2 but not shown in the cross-sectional view of FIG. 4, of reversibly variable transmittance of the device of reversibly variable transmittance of the improved mirror.

In yet another type of improved variable reflectance mirror according to the invention, similar to that illustrated in FIG. 4, the layer of laminating material is not present and electrode-bearing wall 100 is replaced with the prism-shaped piece of material on one surface of which is coated a layer of electrically conducting layer to serve as an electrode of the device of reversibly variable transmittance.

In the improved mirrors of the invention, the angle between the plane of the reflecting means or layer (e.g., layer 18A in FIG. 3 and layer 20 in FIG. 4) and the front surface (e.g., surface 101 in FIG. 3 and surface 221 in FIG. 4) is preferably about 1° to about 5°.

The laminating material, of layer 19 of mirror 300 of FIG. 3 and layer 21 of mirror 400 of FIG. 4, can be any transparent laminating material known in the art. Further, the process of laminating prism-shaped mirror 180 to surface 131 in mirror 300 or prism-shaped solid piece 22 to surface 101, is by any laminating process known in the art. In a preferred improved mirror of the invention, such as mirror 300, characterized by having the reflecting means be the reflecting means of a prism-shaped mirror, surface 131 will be of a piece of glass, solid material element 18 of the prism-shaped mirror will be made of glass and the transparent laminating material will be polyvinyl butyral (PVB). Similarly, in a preferred improved mirror of the invention, such as mirror 400, characterized by having the reflecting means adhered directly to one surface of the device of reversibly variable transmittance and having a prism-shaped piece of solid-material laminated to the surface of the device of reversibly variable transmittance, which is parallel to and spaced-apart from the surface to which the reflecting means is adhered, surface element 101 will be of a piece of glass, the prism-shaped piece of material will be made of glass, and the transparent laminating material will be PVB.

In FIGS. 3 and 4, wall 100, and elements 10 and 10A thereof; wall 130, and elements 13 and 13A thereof; spacer 11; solution space 12; and wire or strip 16 correspond to the same-numbered elements of device 200 illustrated in FIG. 2. Wire or strip 15 in FIGS. 3 and 4 extends to a lead or extension which corresponds to lead 15A shown in FIG. 2.

A mirror of the invention is usually mounted in a frame which shields from view all of the device of reversibly variable transmittance except most of the cross-sectional area (indicated by 14 in device 200 of FIG. 2) of reversibly varied transmittance through which light reflected by the reflecting means of the mirror and seen by the observer of the mirror passes before and after reflecting from the reflecting means. The orientation of the frame can be manually or automatically adjustable. The leads 15A and 16A (illustrated in FIG. 2) of the device will be connected to power supply control elements (e.g., switching means, means for controlling potential difference between the electrodes), which may optionally be located in the frame structure behind the device and the reflecting means or can be completely separate from the frame and mounting, and which, in turn, are connected to a power supply, such as a battery. Said power supply, particularly if small batteries, can also be located in the frame structure; usually, however, the power supply (e.g., an automobile battery) will be located outside the frame. The preferred application of the variable reflectance mirrors of the invention is as anti-glare rearview mirrors for automobiles.

When employed as the variable transmittance component of a variable transmittance light filter, particularly a window, a device of the invention will be framed essentially like a pane of glass in an ordinary window or windshield. All of the device, other than the portion thereof corresponding to most of the cross-sectional area (indicated by 14 in the device 200 of FIG. 2), of reversibly varied transmittance, will be hidden from view by window frame components. Similarly wires from leads, 15A and 16A of the device (illustrated in FIG. 2) will be run inside such frame components, out of the view through the window, to power supply means and power supply control elements outside the window structure.

Display devices can be made with either or both of variable reflectance mirrors and variable reflectance light filters of the invention, wherein devices according to the invention are the variable transmittance components, and which, through variation in reflectance or transmittance, convey information. The area of the device of the invention that transmits or reflects light with variable intensity can be made to have the shape of desired symbols for a display device. Alternatively, separate devices of the invention can be arranged in suitable arrays to have the shape of desired symbols. In one embodiment, as the transmittance of the device or devices is decreased, the symbol represented becomes apparent to the viewer, as the device forms the dark symbol on a light background. In another embodiment, if the symbol is apparent at high transmittance of the device, because the symbol is surrounded by a dark background, activation of the device or devices will decrease transmittance and cause the symbol to fade from view. Virtually any symbol can be displayed with a display device employing a device of the invention as variable transmittance component, including letters, numerals, words, numbers or various designs. Display devices employing the variable transmittance devices according to the invention are also useful in artistic displays, such as stained glass windows with panes of reversibly variable color.

The invention is illustrated in more detail in the following examples.

Unless specified otherwise, all concentrations cited in the examples are at room temperature (20°–27° C.) and all temperatures are in degrees Celsius.

EXAMPLE I

A cell was formed by two sheets of glass 7.6 cm×12.7 cm in area and separated by 0.020 cm thick strips of Nylon monofilament. The sheets of glass had been coated on one side with transparent conductive electrodes of indium-doped tin oxide (ITO), and these sides were placed so as to face each other on the inside of the cell. As illustrated in FIG. 2, the sheets were slightly offset from one another to provide two parallel, narrow, overhanging strips of ITO coating, along the 12.7 cm side of each of the sheets, on opposite sides of the volume for solution. Contacts were made by adhering, with conductive silver epoxy, copper strips along the narrow, overhanging strips of ITO coating and then the edges of the cell were sealed with insulating epoxy. Prior to final sealing, the space between the electrodes was filled with a propylene carbonate solution of 0.05 M N,N,N',N'-tetramethyl-1,4-phenylenediamine, 0.05 M 1,1'-diheptyl-4,4'-bipyridinium difluoroborate and 0.5 M tetra-n-butylammonium fluoroborate.

When 1.0 volts was applied between the electrodes, the solution, which initially appeared colorless, changed to a deep blue-purple color. The solution returned to its bleached, colorless state when the cell was open-circuited or when the cell was short-circuited. The cell returned to its bleached state more rapidly when the polarity of the 1.0 volt potential between the electrodes was reversed for several seconds and then the cell was short-circuited.

When the surface (opposite the ITO-coated surface) of one of the glass sheets was silvered, the device, when viewed through the unsilvered glass side, became a variable reflectance mirror.

EXAMPLE II

A cell that acted as a variable reflectance mirror was formed by two sheets of glass 10.2 cm×10.2 cm in area and spaced by 0.013 cm thick beads of glass. One side of one of the glass sheets was coated with ITO and one side of the other sheet of glass was coated with a vacuum-deposited layer of Inconel metal. The cell was assembled with the ITO and Inconel electrode layers facing each other on the inside of the cell. The copper-strip contacts to the electrode surfaces, sealing and configuration of the device were the same as for the cell in Example I. The space between the electrodes was filled with a solution of 0.02 M 5,10-dihydro-5,10-dimethylphenazine, 0.02 M tetramethylene bis[4(1-benzylpyridine-4'-yl)pyridinium]tetrafluoroborate, and 0.1 M tetra-n-butylammonium fluoroborate in propylene carbonate.

The reflectance from the Inconel electrode rapidly decreased when a potential of 1.0 volts was applied between the ITO and Inconel electrodes. The applied potential caused the solution layer to turn deep blue-green. Removal of the applied potential caused the solution to return to its clear, zero-potential equilibrium condition and the reflectance from the Inconel electrode to increase to the original high level, prior to application of the potential difference.

EXAMPLE III

A device that acted as a variable transmittance light-filter or window was fabricated by spacing two sheets of glass, coated on one side with ITO, 0.013 cm apart, using glass beads for spacing. The dimensions of the sheets of glass were 6.4 cm×25.4 cm. The ITO-coated sides of the sheets were facing. The copper-strip contacts, sealing and configuration of the device were the same as in the device of Example I, with the strips along the 25.4 cm sides of the sheets. The space between the electrodes was filled with a solution of 0.05 M 1,1'-dibenzyl-4,4'-bipyridinium difluoroborate and 0.05 M 5,10-dihydro-5,10-dimethylphenazine in propylene carbonate.

Application of a potential of 1.1 volts between the electrodes, across the solution layer, caused the white light transmittance of the device to decrease from 81.5% to 10.0% in 11 seconds. The steady-state transmittance of the device with 1.1 volts applied was 6.0%. The transmittance of the device, upon short-circuiting the electrodes, increased from 10% back to 70% in a period of 7 seconds and the transmittance increased back to 81.5% within 16 seconds after the electrodes were shorted. The device was cycled 40,000 times at room temperature between its transmittance at zero-applied potential and its steady-state transmittance with 1.1 volts applied between the electrodes. After the 40,000 cycles, the transmittance of the device at zero-applied potential was 78.5% and the steady-state transmittance at 1.1 volts applied potential remained at 6.0%. The speed of changes in transmittance was unchanged by the cycling.

When the device was cycled 20,000 additional times at 55° C., between transmittance at zero applied potential and steady-state transmittance at 1.1 volts, the transmittance at zero-applied potential decreased to 71.5% while that at 1.1 volts remained at 6.0%.

EXAMPLE IV

A device that acted as a variable transmittance light filter or window was fabricated like the device of Example III, except that the space between the electrodes was filled with a solution of 0.04 M 1,1'-di(n-heptyl)-4,4'-bipyridinium difluoroborate, 0.04 M 5,10-dihydro-5,10-dimethylphenazine and 0.1 M tetra-n-butylammonium fluoroborate in propylene carbonate.

Application of a potential of 1.1 volts between the electrodes, across the solution layer, caused the white light transmittance of the device to decrease from 84.5% to 20.0% in a period of 10 seconds. The steady-state transmittance of the device with 1.1 volts applied was 11.0%. The transmittance of the device, upon short-circuiting the electrodes, increased from 20% back to 70% in a period of 7 seconds and the transmittance increased back to 84.5% within 22 seconds after the electrodes were shorted. The device was cycled 40,000 times at room temperature between its transmittance at zero-applied potential and its steady-state transmittance with 1.1 volts applied between the electrodes. After the 40,000 cycles, the zero-applied potential transmittance was 84.0% and the transmittance at 1.1 volts applied potential was 11.0%. The speed of changes in transmittance was unchanged by the cycling.

When the device was cycled 20,000 additional times at 55° C., between transmittance at zero-applied potential and steady-state transmittance at 1.1 volts, the transmittance at zero-applied potential decreased to 77.5% while that at 1.1 volts remained at 11.0%.

EXAMPLE V

A device that acted as a variable transmittance light filter or window was fabricated like the device of example III, except that the dimensions of the sheets of ITO-coated glass were 6.4 cm×7.6 cm. The solution between the electrodes was 0.05 M in 1,1'-dibenzyl-4,4'-bipyridinium difluoroborate and 0.05 M in 5,10-dihydro-5,10-dimethylphenazine in propylene carbonate.

Application of a potential of 1.1 volts between the electrodes, across the solution layer, caused the white light transmittance of the device to decrease from 81.5% to 10.0% in a period of 10 seconds. The steady-state transmittance of the device with 1.1 volts applied was 11.0%. The transmittance of the device, upon short-circuiting the electrodes, increased from 20% back to 70% in a period of 6 seconds and the transmittance increased back to 81.5% within 15 seconds after the electrodes were shorted. The device was cycled 40,000 times at 55° C. between its transmittance at zero-applied potential and its steady-state transmittance with 1.1 volts applied between the electrodes. After the 40,000 cycles, the zero-applied potential transmittance was 65.0% and the steady-state transmittance at 1.1 volts applied potential remained at 6.0%. The speed of changes in transmittance was unchanged by the cycling.

EXAMPLE VI

A device that acted as a variable transmittance light filter or window was fabricated like the device of Example III, except that the space between the electrodes was filled with a solution of 0.01 M N,N,N',N'-tetramethyl-1,4-phenylenediamine, 0.01 M 5,10-dihydro-5,10-dimethylphenazine, 0.01 M 1,1'-dibenzyl-4,4'-bypyridinium difluoroborate, 0.01 M tetramethylene bis[4(1-benzylpyridine-4'-yl)pyridinium]tetrafluoroborate, and 0.1 M tetra-n-butyl ammonium fluoroborate in propylene carbonate.

Application of a potential of 1.2 volts between he electrodes, across the solution layer, caused the white light transmittance of the device to decrease from 84% to 10% in a period of four seconds. Steady-state transmittance with 1.2 volts was 5%. Upon short circuiting of the electrodes, the transmittance of the device increased from 10% to 70% in a period of 6.5 seconds and increased back to the zero-potential equilibrium value of 84% within 15 seconds after the electrodes were shorted.

EXAMPLE VII

Devices, fabricated in essentially the same way as the device illustrated in Example III and filled with propylene carbonate solutions of the electrochromic compound combinations indicated below in Table VII, were found to operate as self-erasing, solution-phase electrochromic devices, similarly to those illustrated in Examples I to VI.

TABLE VII

| ANODIC ELECTROCHROMIC COMPOUND | CATHODIC ELECTROCHROMIC COMPOUND |
|---|---|
| 1. 5,10-dihydro-5,10-dimethylphenazine | 1,1'-di(n-heptyl)-4,4'-bipyridinium difluoroborate |
| 2. 5,10-dihydro-5,10-dimethylphenazine | 1,1'-di(n-heptyl)-4,4'-bipyridinium diperchlorate |
| 3. 5,10-dihydro-5,10-dimethylphenazine | 1,1'-diphenyl-4,4'-bipyridinium difluoroborate |
| 4. 10-methylphenothiazine | 1,1'-di(n-heptyl)-4,4'-bipyridinium difluoroborate |
| 5. 10-ethylphenoxazine | 1,1'-di(n-heptyl)-4,4'-bipyridinium difluoroborate |
| 6. tetrathiafulvalene | 1,1'-dibenzyl-4,4'-bipyridinium difluoroborate |

EXAMPLE VIII

Numerous compounds have been tested for acceptability as anodic or cathodic electrochromic compounds in the single-compartment, self-erasing, solution-phase devices of the invention, with propylene carbonate as solvent.

Some compounds were found to be unacceptable because of instability upon reduction (cathodic compounds) or oxidation (anodic compounds). Such instability is indicated by the absence of any, or the presence of only one, chemically reversible reduction wave (in the case of a cathodic compound) or chemically reversible oxidation wave (in the case of an anodic compound) in a voltammogram, obtained by any standard technique, of the compound in the solvent at room temperature.

No compound, which has at least two chemically reversible voltammographic reduction waves (if a cathodic compound) or at least two chemically reversible voltammographic oxidation waves (if an anodic compound) in a solvent, has been found to lead to unacceptable instability, particularly to cycling, when combined, in a solution in the solvent, with any other compound or compounds with the same property. This observation applies particularly to such combinations which include at least one cathodic compound and at least one anodic compound.

Clearly, to be acceptable, a compound must, upon reduction or oxidation in the solvent, undergo a change in extinction coefficient at least one wavelength in the visible range (4200Å to 7000Å). To insure stability, such a change must occur with the reduction corresponding to the first, of at least two, chemically reversible voltammographic reduction waves, if the compound is a cathodic compound, or the oxidation corresponding to the first, of at least two, chemically reversible voltammographic oxidation waves, if the compound is an anodic compound.

Beyond being minimally acceptable as a cathodic or anodic electrochromic compound in a solution of the invention, a compound will desirably have a solubility, in its zero-potential equilibrium state in the solvent of such a solution, of at least about $10^{-4}$ M at 25° C. and will undergo, at at least one wavelength in the visible range, upon the reduction corresponding to the first chemically reversible voltammographic reduction wave, if a cathodic compound, or the oxidation corresponding to the first chemically reversible voltammographic oxidation wave, if an anodic compound, an increase in extinction coefficient by at least a factor of about $10^2$ to at least about $10^3$ cm$^{-1}$ M$^{-1}$.

Compounds that have been found to meet these criteria of acceptability and desirability, with propylene carbonate as solvent, are all of those specifically mentioned in any of Examples I to VII, and, in addition, the novel anodic compound, N,N',N''-trimethyltriphenazinoxazine, the known anodic compounds, o-tolidine, N,N,N',N'-tetramethylbenzidine, N,N,N',N'-tetraphenyl-1,4-phenylene diamine, and 5,10-dihydro-5,10-diphenylphenazine and the known cathodic compounds 1,1'-dimethyl-4,4'-bipyridinium dichloride, 1,1'-di(p-cyano phenyl)-4,4'-bipyridinium difluoroborate, and 1,1'-diphenyl-4,4'-bipyridinium diiodide.

EXAMPLE IX

This example illustrates that devices of the invention are useful as gray-scale devices, i.e., devices in which, by adjusting potential difference between the electrodes, transmittance can be adjusted to, and stabilized at, intermediate values between the "clear" (i.e., zero-potential equilibrium) value and the darkest value that is possible to attain without impairing chemical stability.

A cell like that of Example III was constructed and filled with a solution which was 0.04 M in 1,1'-di(n-heptyl)-4,4'-bipyridinium difluoroborate and 0.04 M in 5,10-dihydro-5,10-dimethylphenazine in propylene carbonate. The steady-state transmittance of the cell to white light was measured as a function of the potential difference between the electrodes of the device, and the values indicated in Table IX were obtained.

TABLE IX

| Potential between the Electrodes (volts) | Steady-State Transmittance (%) |
|---|---|
| 0.0 | 83 |
| 0.1 | 83 |
| 0.2 | 83 |
| 0.3 | 83 |
| 0.4 | 81.5 |
| 0.5 | 71.5 |
| 0.6 | 56.0 |
| 0.7 | 42.0 |
| 0.8 | 31.0 |
| 0.9 | 24.0 |
| 1.0 | 17.0 |
| 1.1 | 13.0 |
| 1.2 | 11.5 |

EXAMPLE X

A device that acted as a variable reflectance mirror with a thickened solution was fabricated by coating the ITO surface of an ITO-coated piece of glass with a dichloroethane solution of the acrylic sheet material sold under the trademark LUCITE L. Upon evaporation of the dichloroethane, a thin film of acrylic sheet material weighing 0.29 grams was left on the ITO surface. This same piece of glass had a conventional-mirror, silvered coating on the side opposite the ITO-acrylic material side and was used to prepare a cell by spacing the ITO-acrylic side 0.013 cm from the ITO side of a second piece of glass which had only an ITO coating on one side. Spacing was with glass beads. The dimensions of the sheets of glass were 6.4 cm×25.4 cm. The copper-strip contacts, sealing and configuration of the device were the same as that in Example III. The space between the ITO-acrylic side of the one piece of glass and the ITO side of the other piece of glass was filled with a solution of 0.04 M 1,1'-di-n-heptyl-4,4'-bipyridinium difluoroborate, 0.04 M 5,10-dihydro-5,10-dimethylphenazine and 0.1 M tetrabutylammonium fluoroborate in propylene carbonate.

Within several hours at room temperature, the acrylic layer had dissolved in the propylene carbonate solution, resulting in thickening, and the device could be operated as a variable reflectance mirror by varying the potential across the solution between the ITO electrode layers. With an applied voltage of 1.2 volts, the reflectance changed from 73.5% to 20.0% in a period of 2.5 seconds and reached a steady state reflectance of 9.0%. Upon short circuiting the electrodes, the reflectance increased from 9.0% to 60.0% in a period of 17 seconds and eventually increased back to the clear, zero-potential value of 73.5%.

EXAMPLE XI

Synthesis of N,N',N''-trimethyltriphenazinoxazine

The compound was made, starting with the known compounds N-methyltriphenazinoxazine, of Formula

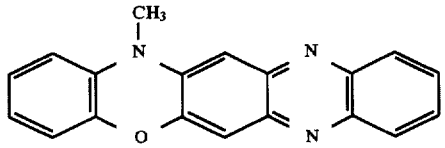

by following the procedure described by Gilman and Dietrich, J. Amer. Chem. Soc. 79, 6178 (1957), for converting phenazine to 5,10-dihydro-5,10-dimethylphenazine. 100 milligrams of the starting compound (0.33 mmoles), 25 milligrams of potassium metal (0.67 mmoles) and 5 ml of ethylene glycol dimethyl ether were stirred for 12 hours. Then an excess of methyl iodide was added, followed by absolute ethanol to destroy excess potassium.

The reaction mixture was then mixed with water. The resulting precipitate was recrystallized from ethanol to yield approximately 2 milligrams of pure product.

In propylene carbonate, the product was found to have chemically reversible oxidation waves and color changes very similar to those of 5,10-dihydro-5,10-dimethylphenazine.

EXAMPLE XII

A device with the configuration illustrated in FIG. 3 was fabricated by laminating, using a standard procedure with the clear laminating material polyvinylbutyral (PVB), an electrochromic device like that in Example III to a conventional, prism-shaped, automobile rearview mirror. The device was filled with a solution of 0.02 M 1,1'-dibenzyl-4,4'-bipyridinium difluoroborate, 0.02 M 5,10-dihydro-5,10-dimethylphenazine, and 0.1 M tetra-n-butylammonium fluoroborate in propylene carbonate. This device was used as the rearview mirror inside an automobile.

During operation, the device provided a distortion-free, continuously variable reflectance (i.e., gray-scale) mirror which was extremely effective in eliminating glare due to headlights on vehicles approaching from behind during night driving.

The device was operated at zero-potential difference when there was little or no glare from headlights of vehicles approaching from behind, 0.6 volts potential difference when there was moderate glare, and 1.0 volts when there was high glare.

The clear state reflectance from the silvered surface of the prism mirror at zero applied potential was greater than 70% of the light incident on the device. The steady state reflectance from the silvered surface at 0.6 volts applied potential was about 30% and at 1.0 volts applied potential the reflectance was about 10%.

Although the invention has been described with some specificity, those of skill will recognize numerous variations and modifications of the specifics that are within the spirit of the invention. The variations and modifications are also within the scope of the invention as disclosed and claimed herein.

What is claimed is:

1. A variable reflectance rearview mirror for a motor vehicle, (A) wherein the variable reflectance is provided by a component of reversibly variable transmittance which is a single-compartment, self-erasing, solution-phase electrochromic device, wherein the solution of reversibly variable transmittance is between and in contact with two planar, parallel, spaced-apart walls, at least one of which is transparent and each of which, on the side in contact with said solution, is coated with an electrode layer of electrically conductive material, wherein the separation between the electrode layers is between about 0.0025 cm and about 0.050 cm, provided that, if one of said walls is not transparent, said non-transparent wall comprises a reflecting layer of high reflectance material which reflects, through said solution and the transparent wall, light which reaches said reflecting layer after entering the solution through the transparent wall, and wherein the solution of reversibly variable transmittance is held in a space defined by said two planar, parallel, spaced-apart walls, and a periphery defined by an epoxy seal in which are embedded glass beads, which are in contact with the sides of said walls, which are in contact with said solution, and which hold apart said walls and (B) wherein, if both of said walls are transparent, the mirror comprises a reflecting layer of high reflectance material which reflects, through the solution of the electrochromic device, light which reaches said reflecting layer after passing through said solution.

2. A mirror according to claim 1 wherein the component of reversibly variable transmittance provides continuously variable reflectance and is gray-scale controllable.

3. A mirror according to claim 2 wherein the reflectance is capable of being reduced from greater than 70% to less than 20% in less than 10 seconds with a potential difference of less than 1.4 volts between the electrode layers of the electrochromic device.

4. A mirror according to claim 1 wherein the reflectance is capable of being reduced from greater than 70% to less than 20% in less than 10 seconds with a potential difference of less than 1.4 volts between the electrode layers of the electrochromic device.

5. A mirror according to any one of claims 2, 3 and 4 wherein, in the one electrochromic device, the solution of variable transmittance comprises:

(A) a solvent;

(B) a cathodic electrochromic compound which, in a voltammogram done in the solvent at room temperature, displays at least two chemically reversible reduction waves, with the first of said reductions accompanied by a increase in molar extinction coefficient at at least one wavelength in the visible range;

(C) an anodic electrochromic compound which, in a voltammogram done in the solvent at room temperature, displays at least two chemically reversible oxidation waves, with the first of said oxidations accompanied by an increase in molar extinction coefficient at at least one wavelength in the visible range; and (D) if all cathodic and anodic compounds in their zero potential equilibrium states are not ionic, an inert current-carrying electrolyte.

6. A mirror according to claim 5 wherein, in the solution of reversibly variable transmittance, the solvent is propylene carbonate.

7. A variable reflectance rearview mirror for a motor vehicle, wherein the variable reflectance is provided by a component of reversibly variable transmittance, which is a single-compartment, self-erasing, solution-phase electrochromic device, wherein the solution of reversibly variable transmittance comprises:

(A) a non-aqueous solvent;

(B) a cathodic electrochromic compound;

(C) 5,10-dihydro-5,10-dimethylphenazine; and (D) if all cathodic compounds in their zero-potential equilibrium states are not ionic, an inert, current-carrying electrolyte.

8. A mirror according to claim 7 wherein, in the electrochromic device, the solution of reversibly variable transmittance is between and in contact with two planar, parallel, spaced-apart walls, at least one of which is transparent and each of which, on the side in contact with said solution, is coated with an electrode layer of electrically conductive material, provided that, if one of said walls is not transparent, said non-transparent wall comprises a reflecting layer of high reflectance material which reflects, through said solution and the transparent wall, light which reaches said reflecting layer after entering the solution through the transparent wall and (B) wherein, if both of said walls are transparent, the mirror comprises a reflecting layer of high reflectance material which reflects, through the solution of the electrochromic device, light which reaches said reflecting layer after passing through said solution.

9. A mirror according to claim 8 wherein the reflectance is capable of being reduced from greater than 70% to less than 20% in less than 10 seconds with a potential difference of less than 1.4 volts between the electrode layers of the electrochromic device.

10. A mirror according to claim 8 wherein the separation between the electrode layers is between 0.0025 and 0.050 cm.

11. A mirror according to claim 10 wherein the reflectance is capable of being reduced from greater than 70% to less than 20% in less than 10 seconds with a potential difference of less than 1.4 volts between the electrode layers of the electrochromic device.

12. A mirror according to claim 8 wherein, in the electrochromic device, the solution of reversibly variable transmittance is held in a space defined by said two planar, parallel, spaced-apart walls, and a periphery defined by an epoxy seal in which are embedded glass beads, which are in contact with the sides of said walls, which are in contact with said solution, and which hold apart said walls.

13. A mirror according to claim 12 wherein the reflectance is capable of being reduced from greater than 70% to less than 20% in less than 10 seconds with a potential difference of less than 1.4 volts between the electrode layers of the electrochromic device.

14. A mirror according to claim 12 wherein the separation between the electrode layers is between 0.0025 and 0.050 cm.

15. A mirror according to claim 14 wherein the reflectance is capable of being reduced from greater than 70% to less than 20% in less than 10 seconds with a potential difference of less than 1.4 volts between the electrode layers of the electrochromic device.

16. A mirror according to claim 7 wherein the component of reversibly variable transmittance provides continuously variable reflectance and is gray-scale controllable.

17. A mirror according to claim 16 wherein the reflectance is capable of being reduced from greater than 70% to less than 20% in less than 10 seconds with a potential difference of less than 1.4 volts between the electrode layers of the electrochromic device.

18. A mirror according to claim 16 (A) wherein, in the electrochromic device, the solution of reversibly variable transmittance is between and in contact with two planar, parallel, spaced-apart walls, at least one of which it transparent and each of which, on the side in contact with said solution, is coated with an electrode layer of electrically conductive material, provided that, it one of said walls is not transparent, said non-transparent wall comprises a reflecting layer of high reflectance material which reflects, through said solution and the transparent wall, light which reaches said reflecting layer after entering the solution through the transparent wall and (B) wherein, if both of said walls are transparent, the mirror comprises a reflecting layer of high reflectance material which reflects, through the solution of the electrochromic device, light which reaches said reflecting layer after passing through said solution.

19. A mirror according to claim 18 wherein the reflectance is capable of being reduced from greater than 70% to less than 20% in less than 10 seconds with a potential difference of less than 1.4 volts between the electrode layers of the electrochromic device.

20. A mirror according to claim 18 wherein the separation between the electrode layers is between 0.0025 and 0.050 cm.

21. A mirror according to claim 20 wherein the reflectance is capable of being reduced from greater than 70% to less than 20% in less than 10 seconds with a potential difference of less than 1.4 volts between the electrode layers of the electrochromic device.

22. A mirror according to claim 18 wherein, in the electrochromic device, the solution of reversibly variable transmittance is held in a space defined by said two planar, parallel, spaced-apart walls, and a periphery defined by an epoxy seal in which are embedded glass beads, which are in contact with the sides of said walls, which are in contact with said solution, and which hold apart said walls.

23. A mirror according to claim 22 wherein the separation between the electrode layers is between 0.0025 and 0.050 cm.

24. A mirror according to claim 23 wherein the reflectance is capable of being reduced from greater than 70% to less than 20% in less than 10 seconds with a potential difference of less than 1.4 volts between the electrode layers of the electrochromic device.

25. A mirror according to claim 12 wherein the reflectance is capable of being reduced from greater than 70% to less than 20% in less than 10 seconds with a potential difference of less than 1.4 volts between the electrode layers of the electrochromic device.

26. A mirror according to any one of claims 1, 7, 9–11, 15–17, 19–21, 29 and 25 wherein, in the solution of reversibly variable transmittance, the solvent is propylene carbonate.

27. A mirror according to any one of claims 7–25 wherein, in the solution of reversibly variable transmittance in its zero-potential equilibrium state, all of the cathodic electrochromic compounds are salts of viologen dications.

28. A mirror according to claim 27 wherein, in the solution of reversibly variable transmittance, the solvent is propylene carbonate.

29. A mirror according to claim 27 wherein, in the solution of reversibly variable transmittance in its zero-potential equilibrium state, the concentration at room temperature of 5,10-dihydro-5,10-dimethylphenazine is between 0.01 and 0.1 molar and the total concentration at room temperature of all of the viologen dications together is between 0.01 and 0.1 molar.

30. A mirror according to claim 29 wherein the viologen dications are selected from the group consisting of 1,1'-dimethyl-4,4'-bipyridinium and 1,1'-dibenzyl-4,4'-bipyridinium.

31. A mirror according to claim 30 the solvent is propylene carbonate.

32. A mirror according to claim 31 wherein the viologen salts are the difluoroborate salts.

33. A variable reflectance rearview mirror for a motor vehicle, wherein the variable reflectance is provided by a component of reversibly variable transmittance, which is a single-compartment, self-erasing, solution-phase electrochromic device, wherein the solution of reversibly variable transmittance comprises:

(A) a non-aqueous solvent;
 (B) a viologen salt; and
 (C) an anodic electrochromic compound which is neutral in its zero-potential equilibrium state.

34. A mirror according to claim 33 wherein the component of reversibly variable transmittance provides continuously variable reflectance and is gray-scale controllable.

35. A mirror according to claim 34 wherein the reflectance is capable of being reduced from greater than 70% to less than 20% in less than 10 seconds with a potential difference of less than 1.4 volts between the electrode layers of the electrochromic device.

36. A mirror according to claim 34 (A) wherein, in the electrochromic device, the solution of reversibly variable transmittance is between and in contact with two planar, parallel, spaced-apart walls, at least one of which said transparent and each of which on the side in contact with said solution, is coated with an electrode layer of electrically conductive material, provided that, if one of said walls is not transparent, said non-transparent wall comprises a reflecting layer of high reflectance material which reflects, through said solution and the transparent wall, light which reaches said reflecting layer after entering the solution through the transparent wall and (B) wherein, if both of said walls are transparent, the mirror comprises a reflecting layer of high reflectance material which reflects, through the solution of the electrochromic device, light which reaches said reflecting layer after passing through said solution.

37. A mirror according to claim 36 wherein the separation between the electrode layers is between 0.0025 cm and 0.050 cm.

38. A mirror according to claim 37 wherein the reflectance is capable of being reduced from greater than 70% to less than 20% in less than 10 seconds with a potential difference of less than 1.4 volts between the electrode layers of the electrochromic device.

39. A mirror according to claim 36 wherein, in the electrochromic device, the solution of reversibly variable transmittance is held in a space defined by said two planar, parallel, spaced-apart walls, and a periphery defined by an epoxy seal in which are embedded glass beads, which are in contact with the sides of said walls, which are in contact with said solution, and which hold apart said walls.

40. A mirror according to claim 39 wherein the reflectance is capable of being reduced from greater than 70% to less than 20% in less than 10 seconds with a potential difference of less than 1.4 volts between the electrode layers of the electrochromic device.

41. A mirror according to claim 39 wherein the separation between the electrode layers is between 0.025 and 0.050 cm.

42. A mirror according to claim 41 wherein the reflectance is capable of being reduced from greater than 70% to less than 20% in less than 10 seconds with a potential difference of less than 1.4 volts between the electrode layers of the electrochromic device.

43. A mirror according to claim 33 (A) wherein, in the electrochromic device, the solution of reversibly variable transmittance is between and in contact with two planar, parallel, spaced-apart walls, at least one of which is transparent and each of which, on the side in contact with said solution, is coated with an electrode layer of electrically conductive material, provided that, if one of said walls is not transparent, said non-transparent wall comprises a reflecting layer of high reflectance material which reaches through said solution and the transparent wall, light which reaches said reflecting layer after entering the solution through the transparent wall and (B) wherein, if both of said walls are transparent, the mirror comprises a reflecting layer of high reflectance material which reflects, through the solution of the electrochromic device, light which reaches said reflecting layer after passing through said solution.

44. A mirror according to claim 43 wherein the reflectance is capable of being reduced from greater than 70% to less than 20% in less than 10 seconds with a potential difference of less than 1.4 volts between the electrode layers of the electrochromic device.

45. A mirror according to claim 43 the separation between the electrode layers is between 0.0025 cm and 0.050 cm.

46. A mirror according to claim 45 wherein the reflectance is capable of being reduced from greater than 70% to less than 20% in less than 10 seconds with a potential difference of less than 1.4 volts between the electrode layers of the electrochromic device.

47. A mirror according to claim 43 wherein, in the electrochromic device, the solution of reversibly variable transmittance is held in a space defined by said two planar, parallel, spaced-apart walls, and a periphery defined by an epoxy seal in which are embedded glass beads, which are in contact with the sides of said walls, which are in contact with said solution, and which hold apart said walls.

48. A mirror according to claim 47 wherein the reflectance is capable of being reduced from greater than 70% to less than 20% in less than 10 seconds with a potential difference of less than 1.4 volts between the electrode layers of the electrochromic device.

49. A mirror according to claim 47 wherein the separation between the electrode layers is between 0.0025 and 0.050 cm.

50. A mirror according to claim 49 wherein the reflectance is capable of being reduced from greater than 70% to less than 20% in less than 10 seconds with a potential difference of less than 1.4 volts between the electrode layers of the electrochromic device.

51. A mirror according to claim 36 wherein the reflectance is capable of being reduced from greater than 70% to less than 20% in less than 10 seconds with a potential difference of less than 1.4 volts between the electrode layers of the electrochromic device.

52. A mirror according to any one of claims 33-51 wherein, in the solution of reversibly variable transmittance, the viologen salts are selected from the group consisting of salts of 1,1'-dimethyl-4,4'-bipyridinium and 1,1'-dibenzyl-4,4'-bipyridinium.

53. A mirror according to claim 52 wherein, in the solution of reversibly variable transmittance in its zero-potential equilibrium state, the solvent is propylene carbonate, the concentration at room temperature of the anodic electrochromic compound is between 0.01 and 0.1 molar and the total concentration at room temperature of all of the viologen dications together is between 0.01 and 0.1 molar.

54. A mirror according to any one of claims 33-51 wherein, in the solution of reversibly variable transmittance, the solvent is propylene carbonate.

55. A variable reflectance rearview mirror for a motor vehicle, (A) wherein the variable reflectance is provided by a component of reversibly variable transmittance which is a self-erasing electrochromic device, wherein the medium of reversibly variable transmittance is between and in contact with two planar, parallel, spaced-apart walls, at least one of which is transparent and each of which, on the side in contact with said medium, is coated with an electrode layer of electrically conductive material, provided that, if one of said walls is not transparent, said non-transparent wall comprises a reflecting layer of high reflectance material which reflects, through said medium and the transparent wall, light which reaches said reflecting layer after entering the medium through the transparent wall, and wherein the medium of reversibly variable transmittance is held in a space defined by said two planar, parallel, spaced-apart walls, and a periphery defined by an epoxy seal in which are embedded glass beads, which are in contact with the sides of said walls, which are in contact with said medium, and which hold apart said walls and (B) wherein, if both of said walls are transparent, the mirror comprises a reflecting layer of high reflectance material which reflects, through the medium of the electrochromic device, light which reaches said reflecting layer after passing through said mediums and wherein the reflectance is capable of being reduced from greater than 70% to less than 20% in less than 10 seconds with a potential difference of less than 1.4 volts between the electrode layers of the electrochromic device.

56. A mirror according to claim 55 wherein the component of reversibly variable transmittance provides continuously variable reflectance and is gray-scale controllable.

57. A variable reflectance rearview mirror for a motor vehicle, wherein the variable reflectance is provided by a component of reversibly variable transmittance, which is a self-erasing electrochromic device having a layer of reflective material which reflects, through said reversibly variable transmittance component of said electrochromic device, light which reaches said reflecting layer after passing through said component, wherein the medium of reversibly variable transmittance comprises:

(A) a non-aqueous solvent;
(B) a viologen salt; and
(C) an anodic electrochromic compound which is neutral in its zero-potential equilibrium state.

58. A mirror according to claim 57 wherein the component of reversibly variable transmittance provides continuously variable reflectance and is gray-scale controllable.

59. A mirror according to claim 58 wherein the reflectance is capable of being reduced from greater than 70% to less than 20% in less than 10 seconds with a potential difference of less than 1.4 volts between the electrode layers of the electrochromic device.

60. A mirror according to claim 58 (A) wherein, it the electrochromic device, the medium of reversibly variable transmittance is between and In contact with two planar, parallel, spaced-apart walls, at least one of which is transparent and each of which, on the side in contact with said medium, is coated with an electrode layer of electrically conductive material, provided that, if one of said walls is not transparent, said non-transparent wall comprises a reflecting layer of high reflectance material which reflects, through said medium and the transparent wall, light which reaches said reflecting layer after entering the medium through the transparent wall and (B) wherein, if both of said walls are transparent, the mirror comprises a reflecting layer of high reflectance material which reflects, through the medium of the electrochromic device, light which reaches said reflecting layer after passing through said medium.

61. A mirror according to claim 60 wherein the reflectance is capable of being reduced from greater than 70% to less than 20% in less than 10 seconds with a potential difference of less than 1.4 volts between the electrode layers of the electrochromic device.

62. A mirror according to claim 60 wherein, in the electrochromic device, the medium of reversibly variable transmittance is held in a space defined by said two planar, parallel, spaced-apart walls, and a periphery defined by an epoxy seal in which are embedded glass beads, which are in contact with the sides of said walls, which are in contact with said medium, and which hold apart said walls.

63. A mirror according to claim 62 wherein the reflectance is capable of being reduced from greater than 70% to less than 20% in less than 10 seconds with a potential difference of less than 1.4 volts between the electrode layers of the electrochromic device.

64. A mirror according to claim 57 (A) wherein, in the electrochromic device, the medium of reversibly variable transmittance is between and in contact with two planar, parallel spaced-apart walls, at least one of which is transparent and each of which, on the side in contact with said medium, is coated with an electrode layer of electrically conductive material provided that, if one of said walls is not transparent, said non-transparent wall comprises a reflecting layer of high reflectance material which reflects, through said medium and the transparent wall, light which reaches said reflecting layer after entering the medium through the transparent wall and (B) wherein, if both of said walls are transparent, the mirror comprises a reflecting layer of high reflectance material which reflects, through the medium of the electrochromic device, light which reaches said reflecting layer after passing through said medium.

65. A mirror according to claim 64 wherein, in the electrochromic device, the medium of reversibly variable transmittance is held in a space defined by said two planar, parallel, spaced-apart walls, and a periphery defined by an epoxy seal in which are embedded glass beads, which are in contact with the sides of said walls, which are in contact with said medium, and which hold apart said walls.

66. A mirror according to any one of claims 57–65 wherein, in the medium of reversibly variable transmittance, the viologen salt is selected from the group consisting of salts of 1,1'-dimethyl-4,4'-bipyridinium and 1,1'-dibenzyl-4,4'-bipyridinium.

67. A variable reflectance rearview mirror for a motor vehicle, which has a range of reflectance from greater than 70% to less than lot and wherein the variable reflectance is provided by a component of reversibly variable transmittance, which is a self-erasing electrochromic device.

68. A mirror according to claim 67, wherein in the electrochromic device the medium of reversibly variable transmittance comprises propylene carbonate.

69. A mirror according to claim 67 wherein the reflectance is continuously variable.

70. A mirror according to claim 67 wherein, in electrochromic device, there is a medium of reversibly variable transmittance which comprises an electrochromic compound in solution.

71. A mirror according to claim 67 which is gray-scale controllable.

72. A mirror according to claim 71 wherein the reflectance is continuously variable.

73. A mirror according to claim 67 wherein, in the electrochromic device, there is a medium of reversibly variable transmittance which is between and in contact with two planar, parallel, spaced-apart walls, each of which, on the side in contact with said medium, is coated with an electrode layer of electrically conductive material, one of which is transparent, and the other of which has as its electrode layer in contact with said medium a reflecting layer of high reflectance material, which reflects, through said medium and the transparent wall, light which reaches said reflecting layer after entering the medium through the transparent wall.

74. A mirror according to claim 73 wherein said high reflectance material is selected from the group consisting of rhodium, silver and inconel.

75. A mirror according to claim 74 wherein the medium of reversibly variable transmittance comprises an electrochromic compound in solution.

76. A variable reflectance rearview mirror for a motor vehicle, wherein the variable reflectance is provided by a component of reversibly variable transmittance, which is a self-erasing electrochromic device, wherein the sheet resistance of a transparent electrode layer is 40 ohms per square or less.

77. A mirror according to claim 76 which is gray-scale controllable.

78. A mirror according to claim 76 wherein the reflectance is continuously variable.

79. A mirror according to claim 76 wherein, in the electrochromic device, there Is a medium of reversibly variable transmittance which comprises an electrochromic compound in solution.

80. A mirror according to claim 76, wherein in the electrochromic device the medium of reversibly variable transmittance comprises propylene carbonate.

81. A mirror according to claim 80 which has a range of reflectance from greater than 70% to less than 10%.

82. A mirror according to claim 76 wherein, in the electrochromic device, there is a medium of reversibly variable transmittance which is between and in contact with two planar, parallel, spaced-apart walls, each of which, on the side in contact with said medium, is coated with an electrode layer of electrically conductive material, one of which is transparent, and the other of which has as its electrode layer in contact with said medium a reflecting layer of high reflectance material, which reflects, through said medium and the transparent wall, light which reaches said reflecting layer after entering the medium through the transparent wall.

83. A mirror according to claim 82 wherein said high reflectance material is selected from the group consisting of rhodium, silver and inconel.

84. A mirror according to claim 83 wherein the medium of reversibly variable transmittance comprises an electrochromic compound in solution.

85. A mirror according to claim 76 which has a range of reflectance from greater than 70% to less than 10%.

86. A mirror according to claim 85 whereon the reflectance is continuously variable.

87. A mirror according to claim 85 which is gray-scale controllable.

88. A mirror according to claim 85 wherein, in the electrochromic device, there is a medium of reversibly variable transmittance which comprises an electrochromic compound in solution.

89. A mirror according to claim 88 wherein in the electrochromic device, the medium of reversibly variable transmittance is between and in contact with two planar, parallel, spaced-apart walls, each of which, an the side in contact with said medium, is coated with an electrode layer of electrically conductive material, one of which is transparent, and the other of which has as its electrode layer in contact with said medium a reflecting layer of high reflectance material, which reflects, through said medium and the transparent wall, light which reaches said reflecting layer after entering the medium through the transparent wall, and which reflectance material is selected from the group consisting of rhodium, silver and inconel.

90. A variable reflectance rearview mirror for an automobile, wherein the variable reflectance is provided by a component of reversibly variable transmittance, which is a self-erasing electrochromic device wherein the medium of reversibly variable transmittance comprises a gel.

91. A mirror according to claim 90 which has a range of reflectance from greater than 70% to less than 10%.

92. A mirror according to claim 90 wherein a transparent electrode layer of the electrochromic device has a sheet resistance of 40 ohms per square or less.

93. A mirror according to claim 90 wherein the medium of reversibly variable transmittance comprises an electrochromic compound in solution.

94. A mirror according to claim 90 wherein, in the electrochromic device, the medium of reversibly variable transmittance is between and in contact with two planar, parallel, spaced-apart walls, each of which, on the side in contact with said medium, is coated with an electrode layer of electrically conductive material, one of which is transparent, and the other of which has as its electrode layer in contact with aid medium a reflecting layer of high reflectance material, which reflects, through said medium and the transparent wall, light which reaches said reflecting layer after entering the medium through the transparent wall.

95. A mirror according to claim 94 wherein said high reflectance material is selected from the group consisting of rhodium, silver and inconel.

96. A mirror according to claim 95 wherein the medium of reversibly variable transmittance comprises an electrochromic compound in solution.

97. A variable reflectance rearview mirror for an automobile, wherein the variable reflectance is provided by a component of reversibly variable transmittances which is a self-erasing electrochromic device wherein the medium of reversibly variable transmittance comprises an acrylic material.

98. A mirror according to claim 98 which has a range of reflectance from greater than 70% to less than 10%.

99. A mirror according to claim 97 wherein a transparent electrode layer of the electrochromic device has a sheet resistance of 40 ohms per square or less.

100. A mirror according to claim 97 wherein the medium of reversibly variable transmittance comprises an electrochromic compound in solution.

101. A mirror according to claim 97 wherein, in the electrochromic device, the medium of reversibly variable transmittance is between and in contact with two planar, parallel, spaced-apart walls, each of which, on the side in contact with said medium, is coated with an electrode layer of electrically conductive material, one of which is transparent, and the other of which has as its electrode layer in contact with said medium a reflecting layer of high reflectance material, which reflects, through said medium and the transparent wall, light which reaches said reflecting layer after entering the medium through the transparent wall.

102. A mirror according to claim 101 wherein said high reflectance material is selected from the group consisting of rhodium, silver and inconel.

103. A mirror according to claim 102 wherein the medium of reversibly variable transmittance comprises an electrochromic compound in solution.

104. A variable reflectance rearview mirror for a motor vehicle, wherein the variable reflectance is provided by a component of reversibly variable transmittance, which is a self-erasing electrochromic device, and wherein, in said electrochromic device, there is a medium of reversibly variable transmittance which is between and in contact with two planar parallel, spaced-apart walls, each of which, on the side in contact with said medium, is coated with an electrode layer of electrically conductive material, one of which is transparent and the other of which has as its electrode layer in contact with said medium a reflecting layer of high reflectance material, which layer reflects, through said medium and the transparent wall, light which reaches said layer after entering the medium through the transparent wall and which reflectance material is selected from the group consisting of rhodium and inconel.

105. A variable reflectance rearview mirror for a motor vehicle, wherein the variable reflectance is provided by a component of reversibly variable transmittance, which is a self-erasing electrochromic device, wherein the medium of reversibly variable transmittance comprises:

(A) a non-aqueous solvent;

(B) a cathodic electrochromic compound;

(C) 5,10-dihydro-5,10-dimethylphenazine; and (D) if all cathodic compounds in their zero-potential equilibrium states are not ionic, an inert, current-carrying electrolyte.

106. A mirror according to claim 105 wherein the component of reversibly variable transmittance provides continuously variable reflectance and is gray-scale controllable.

107. A mirror according to claim 106 wherein the reflectance in capable of being reduced from greater than 70% to less than 20% in less than 10 seconds with a potential difference of less then 1.4 volts between the electrode layers of the electrochromic device.

108. A mirror according to any one of claims 105–107 wherein the cathodic electrochromic compounds are salts of viologen dications.

109. A mirror according to claim 108 wherein the viologen dications are selected from the group consisting of 1,1'-dimethyl-4,4'-bipyridinium and 1,1'-dibenzyl-4,4'-bipyridinium.

* * * * *